(12) United States Patent
May et al.

(10) Patent No.: US 12,203,875 B2
(45) Date of Patent: Jan. 21, 2025

(54) APPARATUS TO DIRECTLY DETECT SOLIDS FORMATION

(71) Applicant: The University of Western Australia, Crawley (AU)

(72) Inventors: Eric Freemantle May, Crawley (AU); Paul Louis Stanwix, Crawley (AU); Matthew Gaven Hopkins, Crawley (AU); Arman Siahvashi, Crawley (AU)

(73) Assignee: The University of Western Australia, Crawley (AU)

( * ) Notice: Subject to any disclaimer, the term of this patent is extended or adjusted under 35 U.S.C. 154(b) by 424 days.

(21) Appl. No.: 17/442,766

(22) PCT Filed: Mar. 27, 2020

(86) PCT No.: PCT/AU2020/050298
§ 371 (c)(1),
(2) Date: Sep. 24, 2021

(87) PCT Pub. No.: WO2020/191451
PCT Pub. Date: Oct. 1, 2020

(65) Prior Publication Data
US 2022/0187219 A1    Jun. 16, 2022

(30) Foreign Application Priority Data

Mar. 28, 2019 (AU) .................. 2019901052

(51) Int. Cl.
*G01N 22/00* (2006.01)
*F25J 1/00* (2006.01)
(Continued)

(52) U.S. Cl.
CPC ............ *G01N 22/00* (2013.01); *F25J 1/0022* (2013.01); *F25J 1/0256* (2013.01); *G01F 1/74* (2013.01); *G01N 33/225* (2013.01); *G01R 33/20* (2013.01)

(58) Field of Classification Search
CPC ...... G01N 22/00; G01N 33/225; F25J 1/0022; F25J 1/0256; G01F 1/74; G01R 33/20
See application file for complete search history.

(56) References Cited

U.S. PATENT DOCUMENTS 6,879,166 B2 *  4/2005  May .................. G01N 22/00
                                              324/636
9,784,046 B2 * 10/2017  Gajji ..................... E21B 19/24
(Continued)

FOREIGN PATENT DOCUMENTS

WO     2015165554 A1    11/2015

OTHER PUBLICATIONS

International Search Report issued in corresponding International Application No. PCT/AU2020/050298, dated Apr. 24, 2020 (6 pages).
(Continued)

*Primary Examiner* — Mohamed Charioui
*Assistant Examiner* — Lynda Dinh
(74) *Attorney, Agent, or Firm* — Osha Bergman Watanabe & Burton LLP

(57) ABSTRACT

An apparatus to directly detect solids formation in a fluid under known pressure and temperature conditions is disclosed. The apparatus includes a vessel having an electromagnetic resonant cavity defined by an upper portion, a lower portion and a gap defined therebetween, the gap having resonant properties sensitive to the presence of a solid phase therein. The upper portion or the lower portion may be provided with a passage extending therethrough in
(Continued)

fluid communication with an inlet to allow ingress of a stream of fluid to the gap and thereby purge solids from the cavity subsequent to solids formation.

The apparatus also includes one or more probes, one or more sensors and a signal processor operatively connected to said sensors and said one or more probes to directly detect solids formation in the fluid within the cavity in response to detected changes in the resonant properties of the cavity.

17 Claims, 11 Drawing Sheets

(51) Int. Cl.
    *F25J 1/02*         (2006.01)
    *G01F 1/74*         (2006.01)
    *G01N 33/22*       (2006.01)
    *G01R 33/20*       (2006.01)

(56) References Cited

U.S. PATENT DOCUMENTS

| | | | | |
|---|---|---|---|---|
| 10,145,830 | B2* | 12/2018 | Fenton | G01K 13/00 |
| 11,579,098 | B2* | 2/2023 | Waters | G01B 15/00 |
| 11,796,362 | B2* | 10/2023 | Theuveny | G01F 1/712 |
| 2003/0155926 | A1 | 8/2003 | May et al. | |
| 2011/0036543 | A1 | 2/2011 | Herzog et al. | |
| 2011/0108457 | A1 | 5/2011 | Da Silva Ferreira Alves et al. | |
| 2015/0075632 | A1* | 3/2015 | Wray | F16L 55/1003 137/13 |
| 2016/0077022 | A1 | 3/2016 | Waglohner et al. | |
| 2017/0167751 | A1* | 6/2017 | Frechette | F24H 1/287 |
| 2018/0178184 | A1* | 6/2018 | Holland | B03C 1/28 |
| 2019/0369149 | A1* | 12/2019 | Dhiman | G01R 27/2635 |
| 2021/0071489 | A1* | 3/2021 | Jamison | B01D 21/262 |

OTHER PUBLICATIONS

Written Opinion of the International Searching Authority issued in corresponding International Application No. PCT/AU2020/050298, dated Apr. 24, 2020 (9 pages).

Office Action issued Chinese Patent Application No. 202080032128.X, mailed on Mar. 1, 2024 (28 pages).

Baker, C.J. et al.; "Rapid Simulation of Solid Deposition in Cryogenic Heat Exchangers To Improve Risk Management in Liquefied Natural Gas Production"; ACS Publications, Energy & Fuels, vol. 32, No. 1, 2018, pp. 255-267 (13 pages).

* cited by examiner

APPARATUS TO DIRECTLY DETECT SOLIDS FORMATION

CROSS-REFERENCE TO RELATED APPLICATIONS

This application is a continuation of International Application No. PCT/AU2020/050298, filed Mar. 27, 2020, incorporated herein by reference.

TECHNICAL FIELD

The disclosure relates to an apparatus to directly detect solids formation in a fluid under known pressure and temperature conditions.

The disclosure also relates to a system and method to prevent or remediate blockages in cryogenic heat exchangers for LNG production.

BACKGROUND

Liquefied natural gas (LNG) is essential in the global trade of natural gas. Liquefaction increases the energy density of natural gas, allowing it to be economically transported over long distance. Natural gas processing and liquefaction is technically demanding as the complexity and variability of composition makes the prediction and understanding of phase equilibrium very difficult. The low temperature and high-pressure conditions required for liquefaction are conducive conditions for freeze out of heavy hydrocarbons. Even at extremely low concentrations, build-up of solids resulting from trace amounts of heavy hydrocarbons are known to be a risk to efficient operation of LNG facilities. Therefore, methods are required to quantify and remediate the risk of solids formation.

Natural gas and gas condensate fluids are primarily composed of low-order alkanes including methane, ethane and propane ($C_1$, $C_2$, and $C_3$). In addition to these components, there are fractional amounts of butanes ($nC_4$, $iC_4$) and heavier hydrocarbons ($C_{5+}$) which present a high risk of freeze-out (Table 1). The exact composition of the $C_{5+}$ group strongly affects the effective freeze-out temperature. Aromatic compounds in particular have a large influence on the freeze-out temperature of the fluid. Conventional analytical methods are unable to efficiently resolve the composition, resulting in overly conservative operation when ($C_{5+}$) impurities are detected.

The risk of solids drop out at the liquefaction stage is typically mitigated through the use of a heavy hydrocarbon (HHC) removal unit that creates a lean natural gas product and heavy waste. A $C_{5+}$ concentration limit (<0.1 mol %) is implemented for the overhead product gas that is monitored via an online gas chromatograph. The location of the $C_{5+}$ monitoring device is typically located after the HHC removal unit and before the liquefaction unit. The concentration limitation has a two-fold benefit in that (1) the LNG product will meet specification for sale and (2) it will avoid freeze-out in main cryogenic heat exchanger (MCHE) downstream. Monitoring the concentration of the $C_{5+}$ group is a measure that allows the online monitoring of heavy hydrocarbon content in dynamic LNG systems, but the lack of transparency into the compositional break down of this group is a limitation that can adversely affect the prediction of freeze-out temperatures.

TABLE 1

Freezing temperature for alkane and aromatic impurities of importance for natural-gas processing.

| Component | Pure Freezing Temperature (° C.) |
| --- | --- |
| Butane ($C_4$) | −140 |
| Pentane ($C_5$) | −129.8 |
| Hexane ($C_6$) | −93.5 |
| Heptane ($C_7$) | −90.6 |
| Benzene | 5.5 |
| p-Xylene | 13.2 |
| Neopentane | −16.6 |
| Cyclohexane | 6.5 |

Inefficient operation of the HHC unit or dynamic composition changes in the reservoir fluids can lead to carryover of HHCs into the MCHE. Due to the large disparity between freezing points of aromatic/cyclic compounds to that of alkanes, carryover on the order of 15 ppm for benzene (67 times less than 0.1 mol %) poses significant solidification risk downstream. FIG. 1 depicts the sensitivity of solid equilibrium temperatures for small ppm concentration increases of benzene in a standard MCHE feed. In this figure the temperature of the MCHE effluent is shown to illustrate the substantial solids drop out risk given the carryover of HHC's, in particular, benzene. An increase in benzene concentration from 10 to 50 ppm shifts the freeze out temperature (solid equilibrium line) 15 K warmer which is well within the operation conditions of the MCHE. This relationship between the HHC concentration and the freeze out temperature is consistent across all trace heavy components. The ability to resolve a complex mixture composition at the ppm level is an increasingly difficult task and one that is both time consuming and expensive.

It is imperative for reliable and efficient operation of the MCHE that the behaviour of the hydrocarbon fluids can be accurately predicted for steady-state and transient conditions. As well as predicting vapour-liquid equilibrium for optimizing LNG production, predicting solid-liquid equilibrium is crucial for avoiding MCHE blockage. Deposition of even small amounts of solid within the tubes of the MCHE, for example during a temporary period of increased $C_{5+}$ concentration, amplifies the risk of a subsequent blockage occurring, since the rate of solids formation and aggregation of other impurities is enhanced by the presence of crystals and surface defects. Even in the case where LNG feed specification is met, over long periods of operation, the accumulation of impurities will increasingly affect the MCHE operation.

Initially, the deposited layer of solids will reduce the thermal efficiency of the heat exchanger, increasing the required refrigerant duty and pressure drop across the unit operation. Ultimately, the pressure drop can become insurmountable and effect the productivity of the whole plant thus requiring shutdown. A case study of this phenomenon is illustrated in FIGS. 2a and 2b, which show the plant data for a 9 month period for Train 4 in the RasGas facility in Qatar (2014). The graphs depict the pressure drop profile as well as the $C_{5+}$ composition and moisture specification of the feed prior to the liquefaction unit. It should be noted that there exists only a single event of $C_{5+}$ composition surpassing specification and no instances of moisture break through. Despite this seemingly innocuous event, over the course of the next few months, the MCHE needed to be shutdown. The timeframe of an unplanned shutdown is such that it negatively impacts contractual supply requirements and consequently it is associated with significant financial penalties.

The discussion of the background to the disclosure is intended to facilitate an understanding of the disclosure. However, it should be appreciated that the discussion is not an acknowledgement or admission that any of the material referred to was published, known or part of the common general knowledge as at the priority date of the application.

SUMMARY

The disclosure provides an apparatus to directly detect solids formation in a fluid under known pressure and temperature conditions. The disclosure also relates to a system and method to remediate solids blockages in cryogenic heat exchangers.

One aspect of the disclosure provides an apparatus to directly detect solids formation in a fluid under known pressure and temperature conditions, the apparatus comprising:

a vessel to receive the fluid, wherein the vessel is provided with means to vary the temperature of the fluid therein, the vessel defining an electromagnetic resonant cavity, operating at frequencies up to and including microwave frequencies, with resonant properties sensitive to the presence of a solid phase;

one or more probes for exciting and monitoring an electromagnetic resonance of the cavity;

a pressure sensor and a temperature sensor for sensing the pressure and temperature respectively of fluid in the cavity; and a signal processor operatively connected to said pressure and temperature sensors and said one or more probes to directly detect solids formation in the fluid within the cavity in response to detected changes in the resonant properties of the cavity;

wherein the electromagnetic resonant cavity is defined by:

an upper portion and a lower portion having a gap defined therebetween, the gap having resonant properties sensitive to presence of a solid phase, wherein the upper portion or the lower portion may be provided with a passage extending therethrough in fluid communication with an inlet to allow ingress of a stream of fluid to the gap and thereby purge solids from the cavity subsequent to solids formation.

In one embodiment, the lower portion is configured to define a well and favour solids formation therein.

In one embodiment, the well is integral with a co-axially aligned spigot extending through the lower portion, the spigot being fabricated from a material having a higher thermal conductivity than a surrounding area of the lower portion, said spigot thereby being capable of providing a thermal gradient between the well and said surrounding area to favour solids formation in the well.

In one embodiment, the lower portion defines a cylindrical side wall, a sloping bottom wall terminating in the well, wherein the well is co-axially aligned with the cylindrical side wall, and the upper portion defines an annular top wall and a protrusion co-axially aligned with the well, wherein said gap is defined between the protrusion and the well.

In one embodiment, the protrusion may comprise a conical protrusion or a cylindrical protrusion.

In one embodiment, the passage may extend through said protrusion. In another embodiment, the passage may extend through the well. The passage extending through said protrusion or the well may be a co-axial passage.

In one embodiment, the passage may be dimensioned to allow the stream of fluid to flow directly to the gap.

In one embodiment, a resonant frequency of said cavity may be tuned by varying the size of the gap. In various embodiments, the gap may be less than 2 mm.

In one embodiment, the annular top wall may be provided with a plurality of apertures defining outlets for egress of the stream of fluid and ports to receive the one or more probes to excite and monitor the electromagnetic response of the cavity.

In one embodiment, the lower portion may be in heat exchange communication with a heat exchanger and/or a thermoelectric cooler to cool the resonant cavity.

In another embodiment, said spigot may be in heat exchange communication with a second heat exchanger and/or thermoelectric cooler. In use, the second heat exchanger may be arranged to cool the well to a lower temperature than the surrounding area of the lower portion.

In one embodiment, said signal processor may be arranged to directly detect solids formation in the fluid within the cavity in response to detected changes to dielectric permittivity ($\Delta\varepsilon$) of the fluid therein.

In one embodiment, changes to dielectric permittivity ($\Delta a$) of the fluid may be calculated according to formula (1):

$$\Delta\varepsilon = \varepsilon_{meas} - \varepsilon_{calc}, \quad (1)$$

wherein, for a known temperature and pressure, $\varepsilon_{calc}$ is a theoretical dielectric permittivity of a bulk fluid, and $\varepsilon_{meas}$ is relative dielectric permittivity and is unitless. $\varepsilon_{meas}$ is calculated according to formula (2):

$$\varepsilon_{meas} = (f_{vacuum}/f_{meas})^2 \quad (2)$$

wherein, for the known temperature and pressure, $f_{vacuum}$ is the electromagnetic resonance frequency of the cavity under vacuum and $f_{meas}$ is the electromagnetic resonance frequency of the cavity in the presence of the fluid.

In one embodiment, the apparatus may be capable of directly detecting the presence of solids in the cavity, wherein the solids occupy about 0.01 v/v % of the cavity. In particular, the apparatus is capable of directly detecting the presence of solids in the cavity, wherein the solids occupy about 0.001 v/v % of the cavity.

In various aspects, the disclosure also provides a system to prevent or remediate solids deposition in a cryogenic heat exchanger.

In one embodiment the system comprises:

a cryogenic heat exchanger for cooling a fluid to a liquid at an operating temperature ($T_{liquid}$), a sensor to directly detect solids formation, wherein said sensor is configured to receive a sample of the fluid cooled, or intended to be cooled, by the cryogenic heat exchanger and determine temperature ($T_{freeze}$) corresponding to a temperature at which solids form in the fluid and $\Delta T_{freeze}$ wherein $\Delta T_{freeze} = T_{liquid} - T_{freeze}$; and, a controller in operative communication with the cryogenic heat exchanger whereby, in use, the controller is arranged to initiate corrective action to avoid solids being deposited in the cryogenic heat exchanger when $\Delta T_{freeze}$ is less than a predetermined operating temperature margin.

In one embodiment, the controller may be arranged to initiate corrective action by raising or lowering the operating temperature ($T_{liquid}$) of the cryogenic heat exchanger or by introducing a remedial fluid in the cryogenic heat exchanger.

In one embodiment the system further comprises:

a means to determine a composition of the fluid; and a thermodynamic simulation program for solid liquid equilibrium (SLE) calculations, said program being arranged to use $T_{freeze}$ and the composition of the fluid as determined by said means to calculate a remedial temperature ($T_{remedial}$) to remove solids deposited in the cryogenic heat exchanger; and a temperature controller in operative communication with the controller to raise or lower the operating temperature of the cryogenic heat exchanger to the remedial temperature ($T_{remedial}$).

In one embodiment, the temperature controller may be in operative communication with the cryogenic heat exchanger to vary a refrigeration duty in one or more locations in the cryogenic heat exchanger to raise or lower the operating temperature to the remedial temperature ($T_{remedial}$).

In an alternative embodiment the system further comprises:
 a means to determine a composition of the fluid; and
 a thermodynamic simulation program for solid liquid equilibrium (SLE) calculations, said program being arranged to use ($T_{freeze}$) and the composition of the fluid as determined by said means to calculate a remedial composition capable of removing solids deposited in the cryogenic heat exchanger; and
a fluid dosing means in operative communication with the controller to introduce the remedial fluid into the cryogenic heat exchanger in an amount sufficient to achieve the remedial composition.

In various embodiments, the sensor to directly detect solids formation may comprise an apparatus comprising an electromagnetic resonant cavity, operating at frequencies up to and including microwave frequencies, with resonant properties sensitive to the presence of a solid phase, as defined above.

In one embodiment the means for determining the composition of the fluid comprises a gas chromatograph.

In one embodiment, said system further comprises a second sensor to directly detect solids formation, as defined above. The second sensor may be arranged in fluid communication with an outlet of the cryogenic heat exchanger to monitor the effectiveness of remediation.

In some embodiments, the second sensor is arranged to receive a sample of output fluid from the outlet of the cryogenic heat exchanger.

In another aspect, the disclosure provides a method of preventing or remediating solids deposition in a cryogenic heat exchanger arranged, in use, to cool a fluid to a liquid at an operating temperature ($T_{liquid}$), the method comprising the steps of:
directly detecting solids formation in a sample of fluid cooled by, or intended to be cooled by, the cryogenic heat exchanger and determining temperature ($T_{freeze}$) corresponding to a temperature at which solids form in the fluid and $\Delta T_{freeze}$ wherein $\Delta T_{freeze}=T_{liquid}-T_{freeze}$; and
initiating corrective action for operating the cryogenic heat exchanger when $\Delta T_{freeze}$ is less than a predetermined operating temperature margin.

In one embodiment, initiating corrective action comprises raising or lowering the operating temperature ($T_{liquid}$) of the cryogenic heat exchanger.

In an alternative embodiment, initiating corrective action comprises introducing a remedial fluid into the cryogenic heat exchanger.

In one embodiment, the method further comprises the steps of:
determining a composition of the fluid;
performing solid liquid equilibrium (SLE) calculations using ($T_{freeze}$) and the composition of the fluid as determined to calculate a remedial temperature ($T_{remedial}$) to remove solids deposited in the cryogenic heat exchanger; and,
raising or lowering the operating temperature of the cryogenic heat exchanger to the remedial temperature ($T_{remedial}$).

In an alternative embodiment, the method further comprises the steps of: determining a composition of the fluid;
performing solid liquid equilibrium (SLE) calculations using ($T_{freeze}$) and the composition of the fluid as determined to calculate a remedial composition capable of dissolving solids deposited in the cryogenic heat exchanger; and,
adjusting the composition of the fluid in the cryogenic heat exchanger to the remedial composition.

In one embodiment, the step of detecting solids formation may be performed by using an apparatus for detecting solids formation as defined above.

In one embodiment, adjusting the composition of the fluid comprises injecting an amount of a remedial fluid into the fluid. In one example, the remedial fluid may comprise one or more hydrocarbon compounds capable of increasing a solubility of the solids deposited in the cryogenic heat exchanger.

In one embodiment, the method further comprises monitoring effectiveness of remediation by sampling output fluid from the cryogenic heat exchanger and testing said output fluid for solids formation.

In another embodiment, prior to taking remedial steps comprising raising or lowering the operating temperature of the cryogenic heat exchanger to the remedial temperature $T_{remedial}$ and/or adjusting the composition of the fluid in the cryogenic heat exchanger to the remedial composition, said method comprises testing said remedial steps in the apparatus for detecting solids formation as defined above.

BRIEF DESCRIPTION OF DRAWINGS

Notwithstanding any other forms which may fall within the scope of the process as set forth in the Summary, specific embodiments will now be described with reference to the accompanying figures below:

FIG. 10 b) is a graphical representation of benzene solubility as a function of the volume of three different remedial fluids, mixed refrigerant (MR); iso-butane ($iC_4$); and normal-pentane ($n-C_5$).

DESCRIPTION OF EMBODIMENTS

Figure 1:
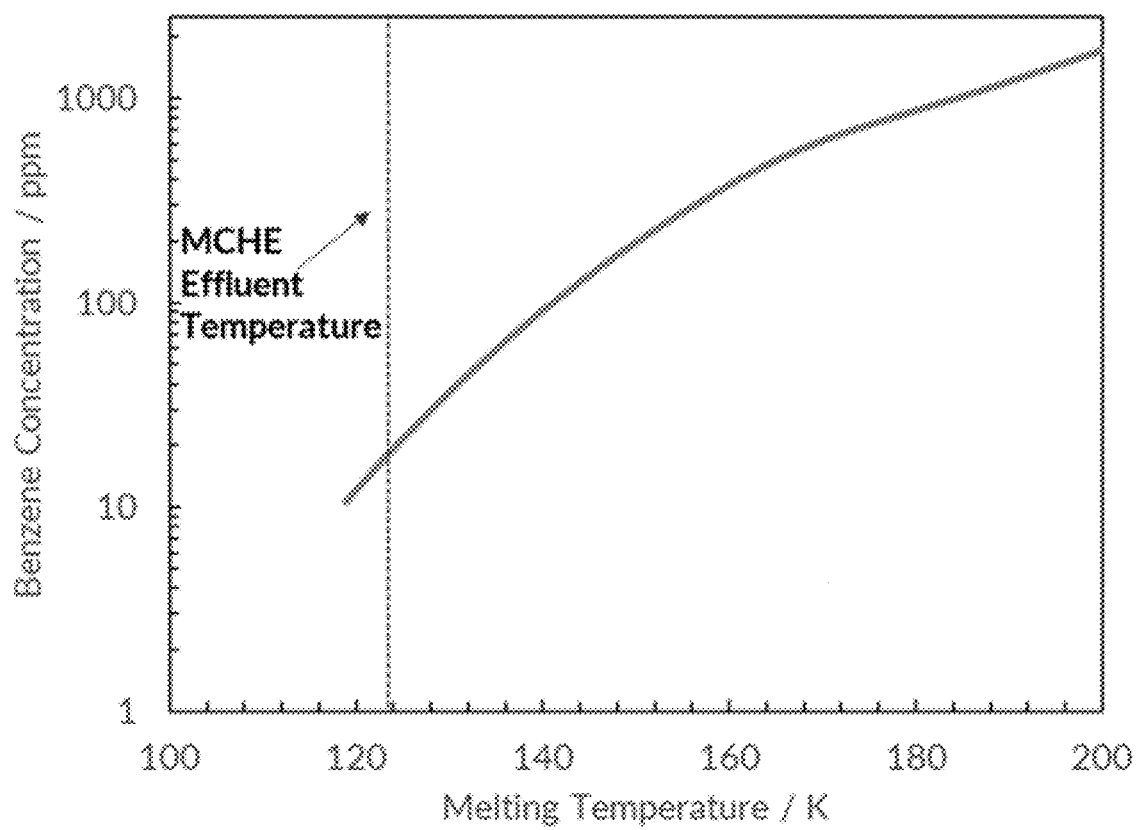
FIG. 1 is a phase diagram of solid-liquid equilibrium for varying molar concentrations of benzene in a natural gas fluid under temperature conditions of a conventional cryogenic heat exchanger.
Figure 2A:
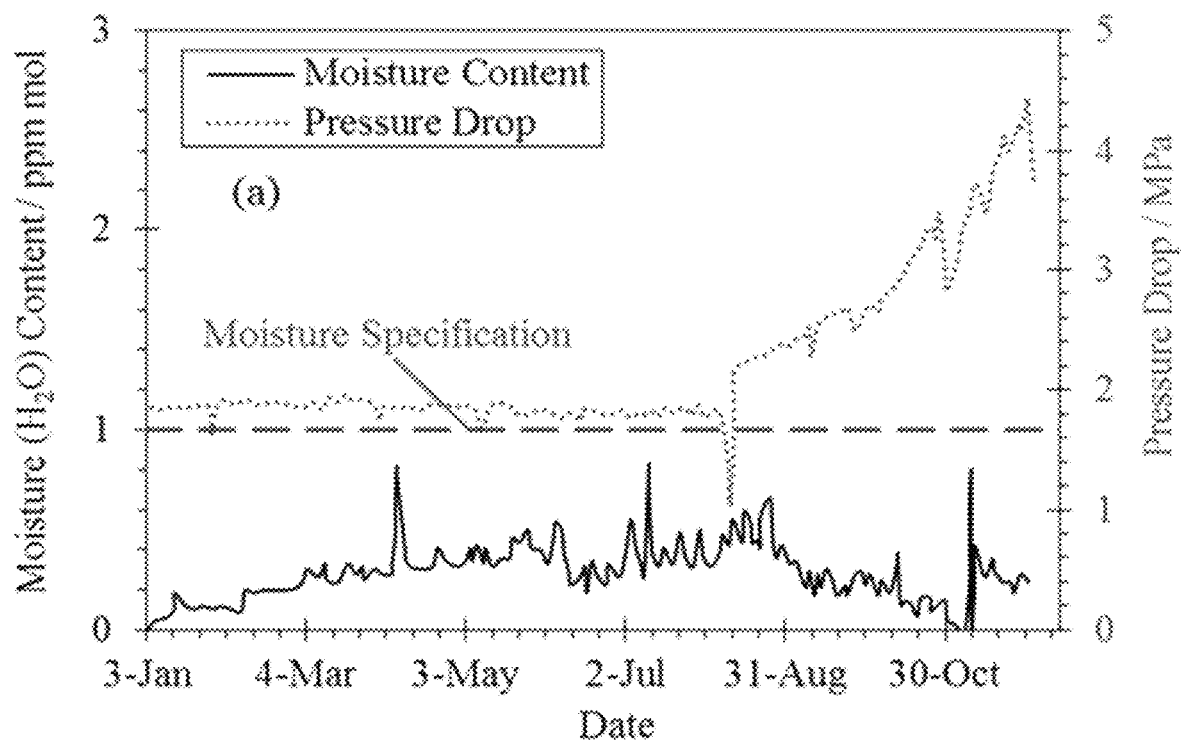
FIGS. 2a and 2b are graphical representations of moisture and $C_{5+}$ content, respectively, together with measured pressure drop in the RasGas Train 4 recorded over a nine (9) month period.
Figure 2B:
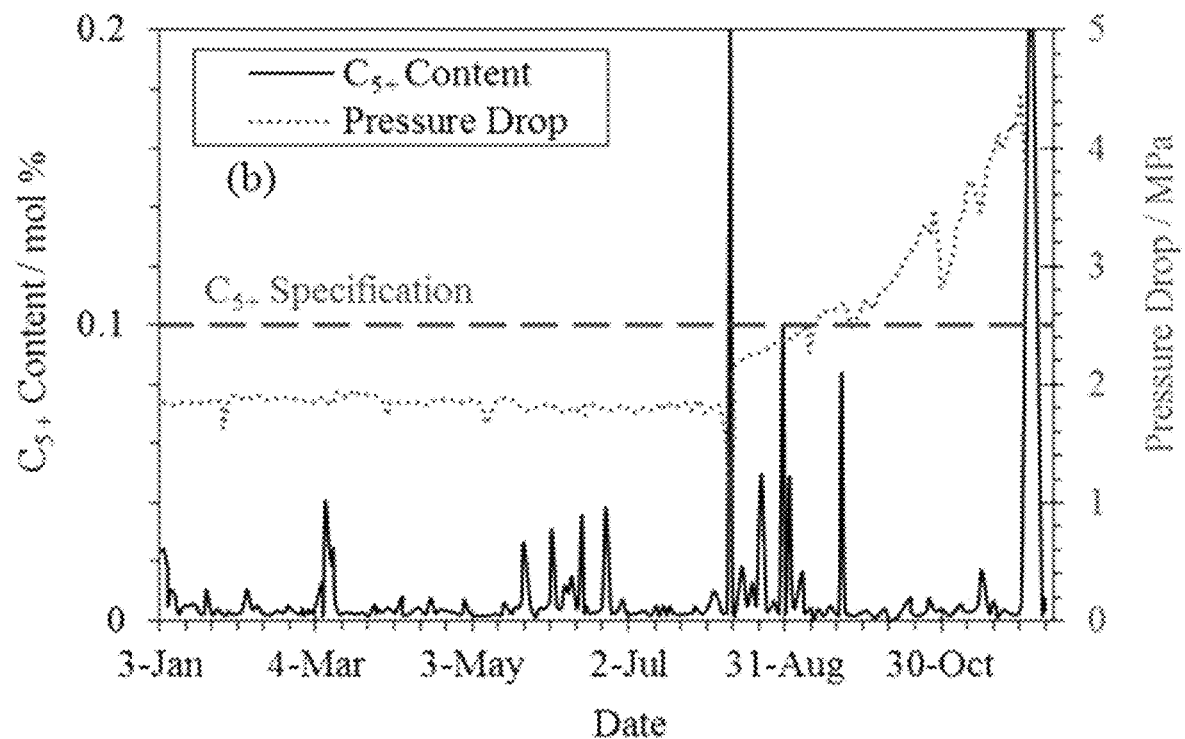

The disclosure relates to an apparatus and method for detecting solids formation, in particular an apparatus and method for detecting solids formation in cryogenic heat exchangers, such as cryogenic heat exchangers used for LNG production. The disclosure also relates to a system and method for remediating blockages in cryogenic heat exchangers.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

The term "about" as used herein means within 5%, and more preferably within 1%, of a given value or range. For example, "about 3.7%" means from 3.5 to 3.9%, preferably from 3.66 to 3.74%. When the term "about" is associated with a range of values, e.g., "about X % to Y %", the term "about" is intended to modify both the lower (X) and upper (Y) values of the recited range. For example, "about 20% to 40%" is equivalent to "about 20% to about 40%".

Specific Terms

A solid is a fundamental state of matter in which atoms or molecules are closely packed together in a regular geometric lattice (crystalline solids) or irregularly (amorphous solids) and contain the least amount of kinetic energy. The term 'solids formation' as used herein refers to solids arising from a phase transition, such as a gas to solids phase transition or a liquid to solids phase transition, whereby the phase transition is caused by a change in pressure and/or temperature, in particular a decrease in temperature.

The phrase "directly detect solids formation" as used herein refers to the ability to sense or measure a change in a physical property caused by the presence of solids arising from a phase transition. Direct detection of solids formation may be distinguished from indirect detection of solids formation whereby an apparatus, instrument or sensor is capable of measuring or sensing a physical property, such as temperature or pressure, at which solids are predicted or anticipated to form as a result of phase transition.

The term "cryogenic" when used herein to describe a heat exchanger refers to heat exchanger configured to operate at very low temperatures (from about −140° C. and below) for the purposes of liquefying one or more gases. Such cryogenic heat exchangers are commonly used for liquefied natural gas (LNG) production, and production of liquid gases, such as liquid nitrogen, liquid oxygen, liquid hydrogen, liquid helium and liquid argon.

The term "fluid" as used herein refers to a homogenous gas mixture or a homogenous liquid mixture, optionally with one or more trace impurities. A "trace impurity" is a compound having a concentration in the fluid of less than or equal to 3000 ppm.

The trace impurity may be a "freezable compound", in other words a compound capable of forming a solid at a higher temperature than a phase transition temperature of the fluid. Examples of freezable compounds in a fluid such as natural gas include, but are not limited to, water, sour gases such as carbon dioxide and hydrogen sulphide, carbon disulphide, carbonyl sulphide, mercaptans (R—SH, where R is an alkyl group having one to 20 carbon atoms), sulphur dioxide, aromatic sulphur-containing compounds, and heavy hydrocarbons including aromatic hydrocarbons such as benzene, toluene, xylene, naphthalenes, and so forth. The term 'heavy hydrocarbon' as used herein may be referred to by the symbol '$C_{5+}$' and refers to hydrocarbons having a carbon chain or skeleton of five (5) or more carbon atoms. Other examples of freezable compounds may include waxes.

It will also be understood by those skilled in the art that two or more compounds may potentially combine to form a clathrate which may be also be a "freezable compound". For example, methane hydrate is a clathrate comprising methane and water which solidifies at a higher temperature that the solids formation temperature of methane or water.

The term "bulk fluid" as used on its own or in conjunction with "composition" or "properties" refers to the fluid excluding the one or more trace impurities or the composition or properties of the fluid in the absence of the one or more trace impurities.

The term "operating temperature margin" as used herein with respect to a cryogenic heat exchanger refers to a permitted variance in temperature at which the cryogenic heat exchanger may be operated. The permitted variance may vary according to the size and type of cryogenic heat exchanger and the bulk fluid composition of the fluid cooled in the cryogenic heat exchanger, and may be predetermined with a thermodynamic simulation program for solid liquid equilibrium (SLE) calculations (as will be described below).

The term 'remedial fluid' as used herein may refer to a gas or a liquid comprising a compound or a mixture of two or more compounds capable of removing the solids deposited in the cryogenic heat exchanger. The one or more compounds in the remedial fluid may be capable of increasing the solubility of the solids in the fluid passing through the cryogenic heat exchanger by varying the composition of the fluid. Alternatively, the one or more compounds in the remedial fluid may be capable of moving the conditions of solid-liquid equilibrium in the cryogenic heat exchanger such that the solids undergo a solid-liquid or solid-gas phase transition. In some examples, the one or more compounds may be hydrocarbon compounds.

Apparatus to Directly Detect Solids Formation

Embodiments described herein generally relate to an apparatus to directly detect solids formation in a fluid. In particular, various embodiments relate to an apparatus configured to detect solids formation in a fluid comprising freezable compounds.

While the disclosure is made in the context of LNG production, it will be appreciated that the disclosure has general application in the cryogenic production of other gases and liquids where it is undesirable for impurities in said fluids to form solids. Other examples where the apparatus as described herein may have a general principle of application include, but are not limited to, cryogenic production of liquid gases such as nitrogen, argon, hydrogen or helium; determination of hydrate formation temperatures in gas (and oil) production systems; determination of wax formation temperatures in gas (and oil) production and so forth.

Referring to FIGS. 3a-3d, where like numerals refer to like features throughout, there are shown various embodiments of an apparatus 10 for directly detecting solids formation. The apparatus 10 includes a cylindrical pressure vessel 12 comprising a lower portion 14 sealingly coupled to an upper portion 16 with a plurality of fasteners 18 and a sealing member 20, such as an O-ring. In use, the lower and upper portions 14, 16 define an electromagnetic resonant cavity 22. The electromagnetic resonant cavity 22 operates at frequencies up to and including microwave frequencies, with resonant properties sensitive to the presence of a solid phase as will be described later.

With regard to the electromagnetic resonant cavity 22, the lower portion 14 defines a cylindrical side wall 24 and a sloping bottom wall 26 terminating in a co-axially aligned flat-bottomed well 28. The upper portion 16 defines an annular top wall 30 and a conical protrusion 32 extending into the cavity 22 terminating in a flat surface 34 co-axially aligned with the flat-bottomed well 28, with a gap 36 therebetween of 2 mm or less. It will be appreciated that the size of the gap 36 is selected to be a balance between sensitivity (which is enhanced by a smaller gap) and robustness in operation. Too small a gap may become fouled or blocked by small solid metal particles that may have passed through upstream filters. Additionally, the stability of the baseline frequency (i.e. frequency under vacuum conditions) of the resonant cavity 22 may become adversely affected by vibrations or drift in the gap dimension over time. In one embodiment, the gap 36 may be from 0.1 mm to 2 mm.

Freezing is a stochastic phenomenon which may be manifest by thermal and compositional driving forces as well as the presence of favourable nucleation sites. In various embodiments, the resonant cavity 22 is configured to favour solids formation in the well 28. For example, the respective angles of inclination of the sloping bottom wall 26 and the conical protrusion 32 are arranged to promote the flow of fluids towards the well 28. Similarly, respective joins between the cylindrical side wall 24 and the sloping bottom wall 26 of the lower portion 14 and the annular top wall 30 and the conical protrusion 32 of the upper portion 16 may be curved or bevelled to avoid stagnant regions and promote flushing of the resonant cavity 22. It will also be appreciated that respective surfaces of the sloping bottom wall 26 and the conical protrusion 32 may be highly polished to deter solids formation thereon.

Further, the lower portion 14 may be fabricated from a thermally conductive material, such as stainless steel or aluminium. It may be advantageous for the thermally conductive material in the well 28 or proximal thereto to have the same or similar material properties as relevant portions of cryogenic equipment, such as a cryogenic heat exchanger. In the embodiment shown in FIG. 3a, for example, the lower portion 14 is provided with a spigot 28a extending therethrough in co-axial alignment with the conical protrusion 32, wherein a leading face of the cylindrical spigot 28a defines the well 28. The spigot 28a may be fabricated from a different thermally conductive material than the lower portion 14, such as copper. In particular, the spigot 28a may be fabricated from a material with a higher thermal conductivity than the lower portion 14, in particular a portion of the lower portion 14 surrounding the well 28. The difference in thermal conductivities between the lower portion 14 and said spigot 28a amplifies the temperature gradient therebetween, creating a localised 'cold spot' in the well 28 where solids preferentially form. In other words, it is possible to establish a thermal gradient between the well 28 and the surrounding area to favour solids formation in the well 28.

The lower portion 14 may also be provided with means to control the temperature thereof so that solids formation in the well 28 is favoured. For example, the lower portion 14 may be in heat exchange communication with a liquid nitrogen heat exchanger (not shown). Such liquid nitrogen cooling allows the resonant cavity 22 to be cooled to temperature conditions comparable to cryogenic gas processing conditions (e.g. 90-130 K). In some embodiments the liquid nitrogen heat exchanger may be in combination with resistive heating to control the temperature of the electromagnetic resonant cavity 22.

Additionally, or alternatively, the apparatus 10 may be provided with a thermoelectric cooler, such as a Peltier device, to cool the lower portion 14, in particular proximal to the well 28, to a desired temperature range.

Said spigot may also be arranged in heat exchange communication with a second heat exchanger and/or thermoelectric cooler (not shown). The second heat exchanger and/or thermoelectric cooler may be arranged, in use, to cool the well 28 to a lower temperature than the portion of the lower portion 14 surrounding the well 28.

In some embodiments, resistive heating may also be provided to the cylindrical side wall 24 of the cavity 22 to establish a thermal gradient therein and ensure that the well 28 is 'colder' than any other region of the cavity 22. The arrangement described in these particular embodiments is useful in the absence of the spigot 28a as described above.

The lower portion 14 may be provided with a plurality of calibrated thermometers or thermistors, such as a platinum probe, which may be located with respect to the resonant cavity to monitor temperature therein. For example, a first thermistor 38 may be disposed in the lower portion 14 proximal to the well 28 and may be used to infer temperature ($T_{freeze}$) at which solids form. A second thermistor 40 may be disposed proximal the cylindrical side wall 24 to measure the magnitude of a temperature gradient present in the resonant cavity 22. A further thermistor 42 may also be provided in a base of the lower portion 14 to monitor a control temperature of the apparatus 10.

Figure 3A:
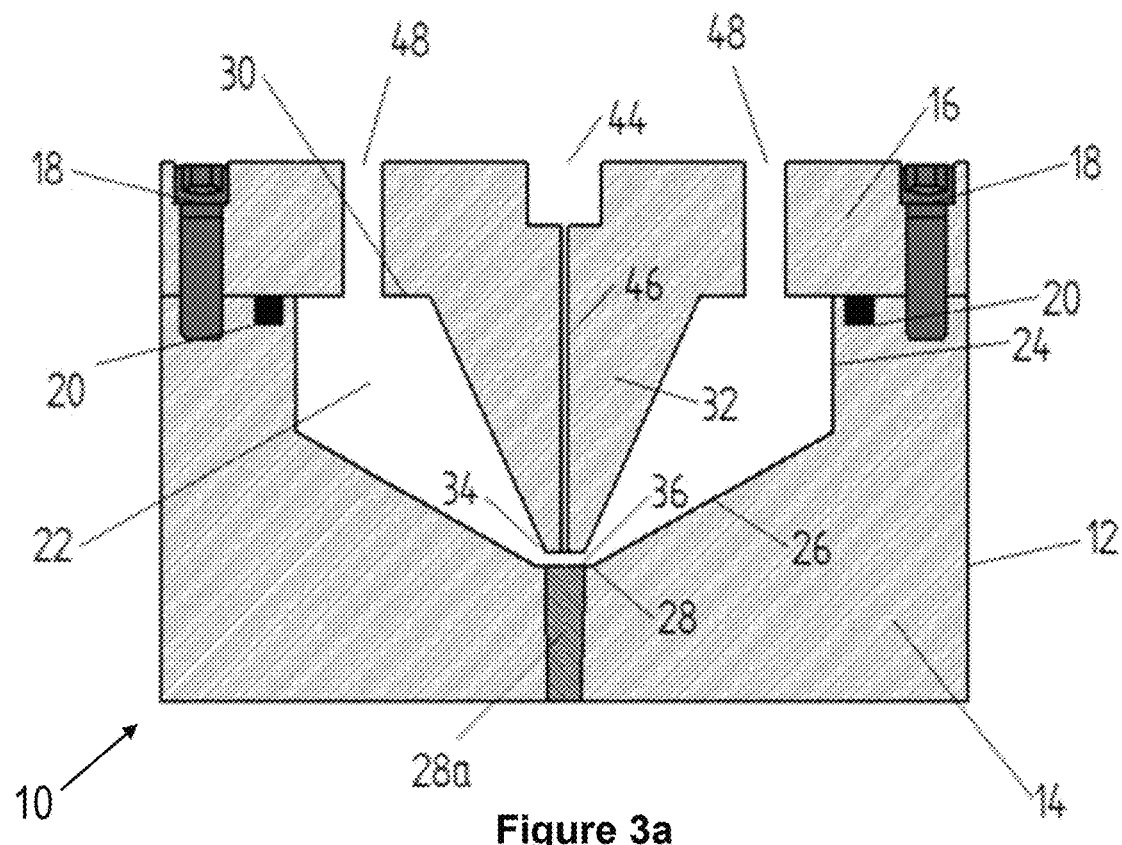
FIGS. 3a and 3b are orthogonal cross sectional representations of one embodiment of an apparatus for directly detecting solids formation and FIGS. 3c and 3d are cross sectional representations of alternative embodiments of the apparatus for directly detecting solids formation.
Figure 3B:
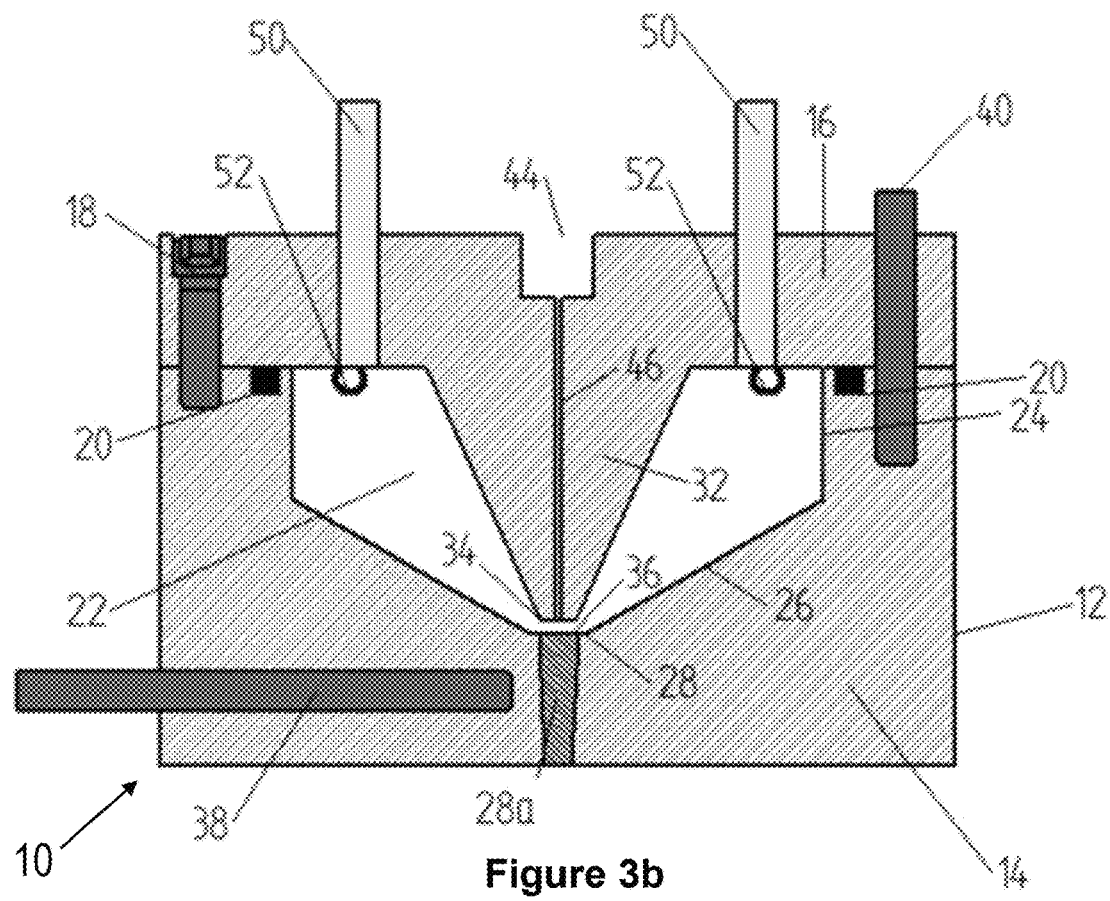

In one embodiment, as shown in FIG. 3a, the conical protrusion 32 of the upper portion 16 is provided with an inlet 44 in fluid communication with a co-axial passage 46 extending therethrough to allow samples of fluid to enter the electromagnetic resonant cavity 22 for investigation of their phase behaviour and measurement of $T_{freeze}$. The passage 46 may be dimensioned to allow fluid flow directly to the gap 36 without impacting the electromagnetic field distribution within the cavity 22.

Figure 3C:
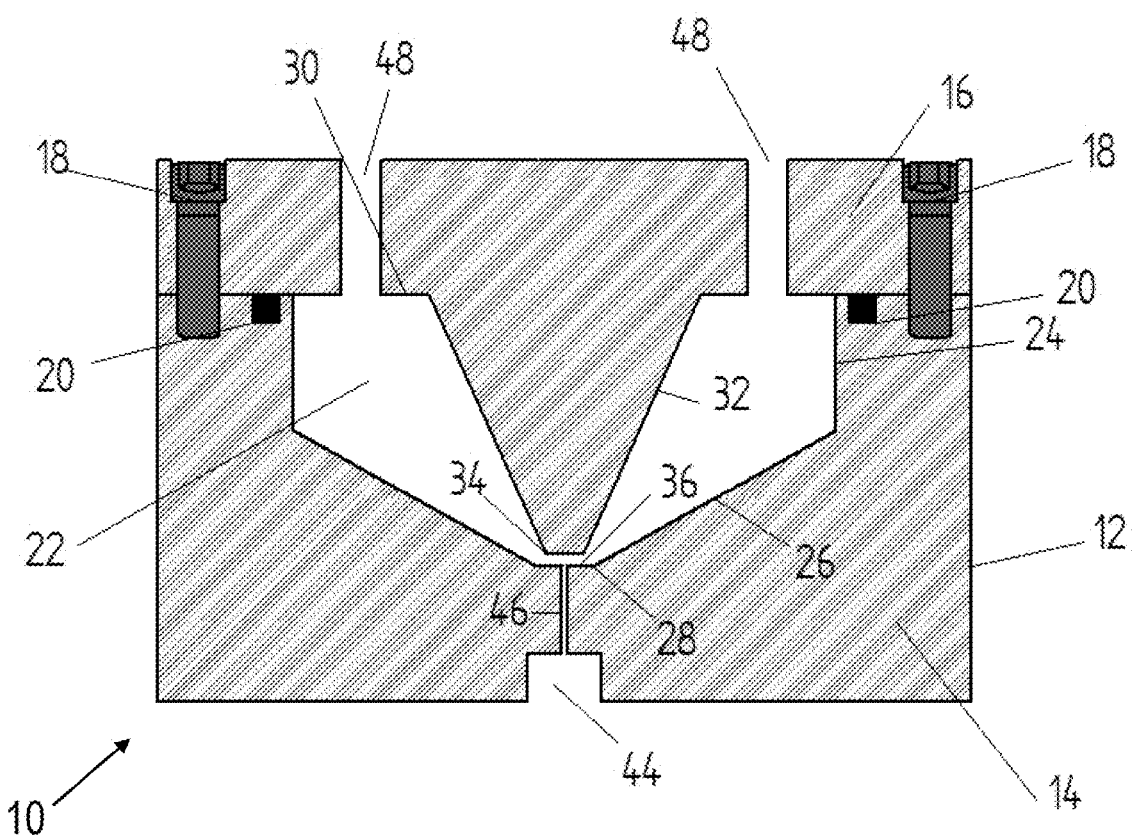
Figure 3D:
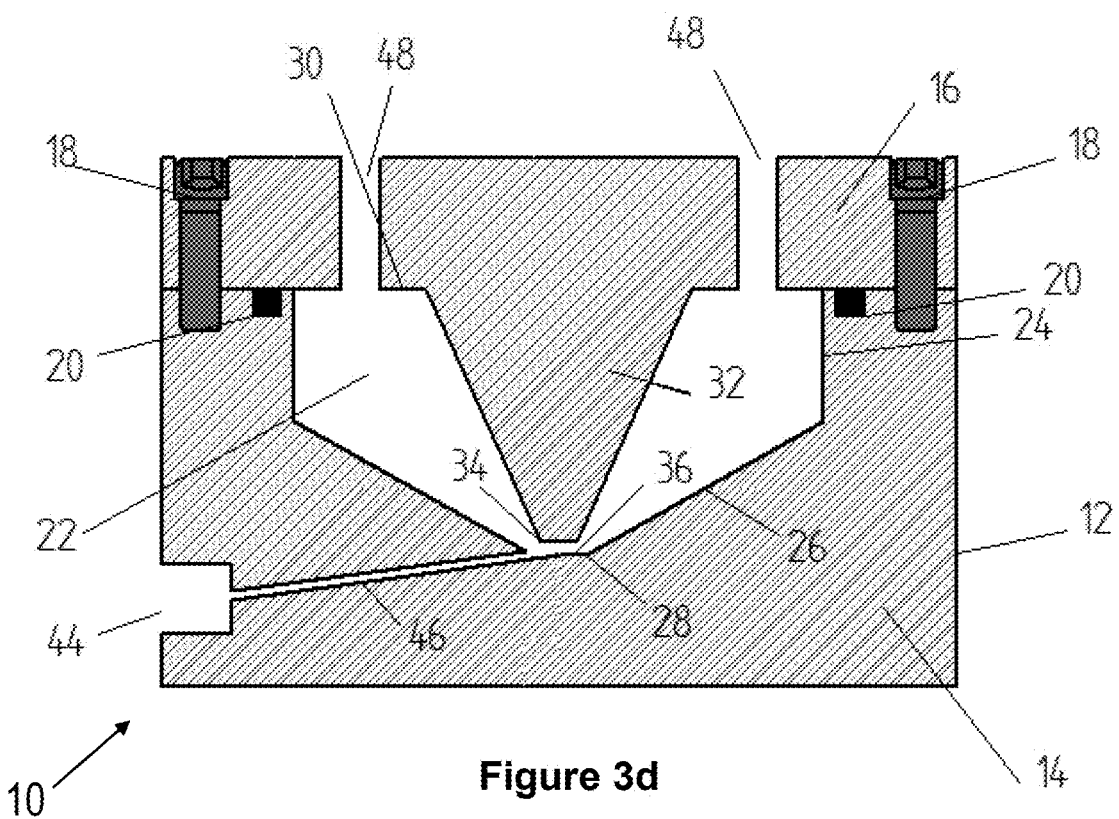

In alternative embodiments, as shown in FIGS. 3c and 3d, the inlet 44 is disposed in the lower portion 14. The passage 46 is disposed in fluid communication with the inlet 44 and extends through the lower portion 14. In the embodiment shown in FIG. 3c, the passage 46 extends co-axially with respect to the well 28.

Advantageously, the passage 46 terminates at the gap 36 between the well 28 and the flat surface 34 of the conical protrusion 32, thereby allowing ingress of a stream of fluid to purge solids from the gap 36 subsequent to solids formation. In this way, the cavity 22 may efficiently recover to baseline conditions following a solids formation detection event.

The annular top wall 30 of the upper portion 16 is also provided with a plurality of apertures defining outlets 48 for egress of the fluid and ports 50 to receive one or more microwave probes 52 to excite and monitor an electromagnetic response of the cavity 22. The microwave probes 52 may include any suitable electromagnetic resonance sensor including, but not limited to, a frequency discriminator circuit (separate to or integral to an oscillator circuit), radiofrequency (RF) source and power detector, or a network analyser. Electromagnetic signals may be transmitted through or reflected from the resonant cavity 22 via sites located in regions of suitable field strength. Accordingly, it is possible to measure resonance frequency via transmission or reflection modes of operation. In a preferred embodiment, the resonance frequency is measured by transmission because the signal quality is better. However, it should be noted that the transmission mode requires two seals, whereas reflection mode requires one seal. Consequently, the reflection mode is more robust from the perspective of a reduced probability that a leak of high pressure fluid within the cavity 22 may occur.

The apparatus 10 may be in operative communication with a processor and a controller (not shown) which are used for data acquisition, resonant frequency measurement, thermal control, flow control, and to generate real time data analysis of key parameters including, but not limited to, resonance frequency, temperature and pressure.

The gap 36 between the flat surface 34 of the conical protrusion 32 and the well 28 defines a capacitive region whereby the electrical field therein is concentrated, thereby making the resonant frequency of said cavity 22 highly sensitive to the dielectric permittivity (E) of material in the gap 36. It will be appreciated by those skilled in the art that the frequency of the resonant cavity 22 may be tuned by varying the size of the gap 36.

The measured resonant frequency (f) is related to E according to the $$f_0 = \frac{f_{vac}}{\sqrt{\varepsilon}}$$

where the vacuum frequency ($f_{vac}$) is determined by the geometry of the cavity 22.

Various electromagnetic models, analytic and/or numerical in nature can be used to predict the resonant modes of the cavity 22. For example, in this particular embodiment, finite element analysis (FEA) may be used to solve electromagnetic field equations, allowing the frequency response to changes in dielectric permittivity (for example as associated with a fluid-phase transition) to be accurately modelled.

The geometry of the embodiment described with reference to the figures exhibits a first resonant mode at ~2.6 GHz in vacuum. The electric field distribution of this mode exhibits high electrical intensity between the conical protrusion 32 and the well 28 in the gap 26. The frequency measured with this mode is almost entirely determined by the dielectric properties of the fluid (or solid) in this region. FEA has shown that the presence of small amounts of solids in the gap 26 can generate a signal response that can be resolved and detected.

Figure 4:
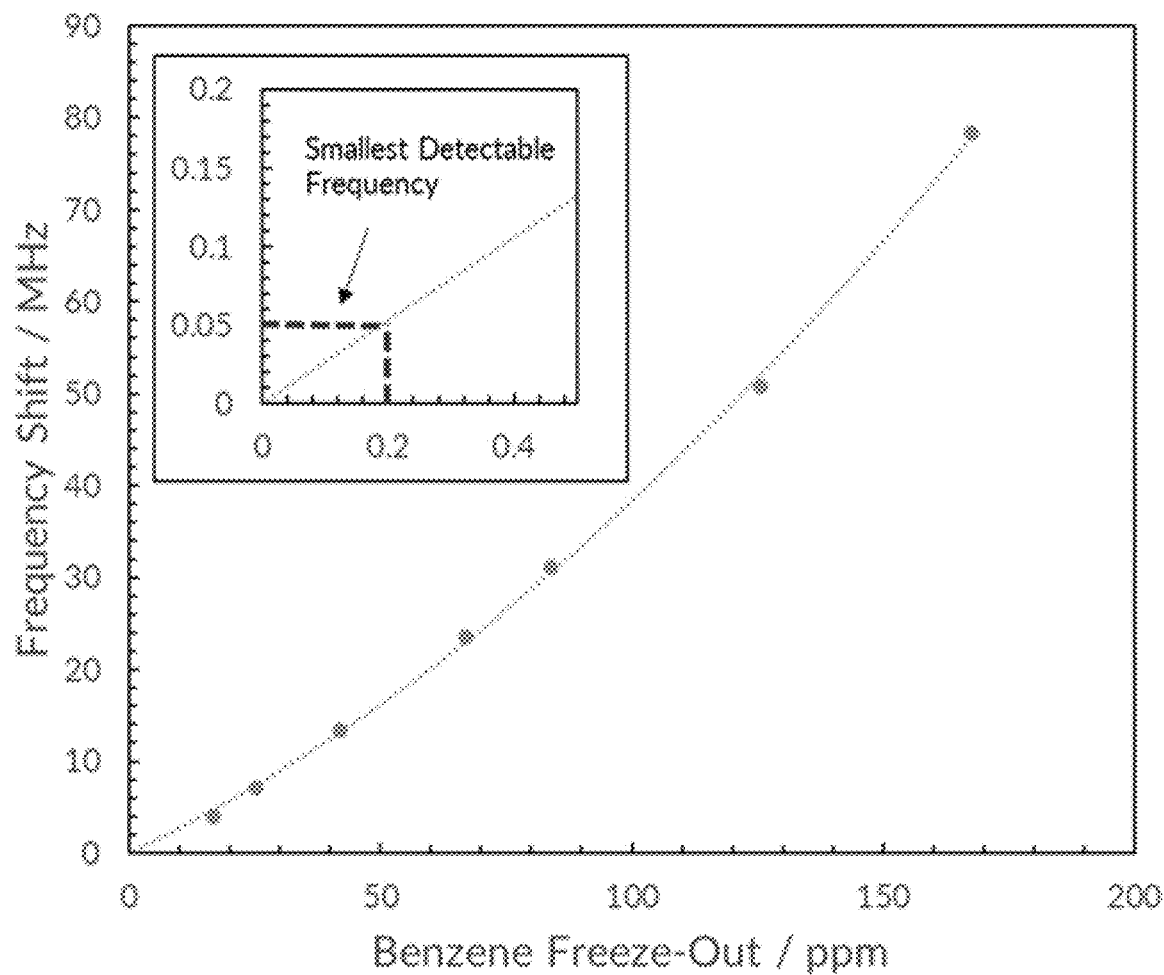
FIG. 4 is a graphical representation of a Finite Elemental Analysis (FEA) simulation of frequency responses for one embodiment of the apparatus as described herein with respect to varying amounts of benzene solids formation in LNG.

For example, a FEA simulation of benzene freeze-out in LNG is capable of predicting the smallest detectable volume of solids in the well 28. FIG. 4 illustrates the expected frequency shift given varying amounts of benzene present in the gas sample when cooled in the well 28 of the cavity 22 until benzene solidifies. Extrapolation of the trend line suggests that the presence of only 1 ppm benzene could cause a detectable 50 kHz shift in resonant frequency. Example 1 (described later) illustrates the ability to detect solids occupying as little as 0.0001 v/v % of the volume of cavity 22.

In use, a stream of fluid may be passed into the electromagnetic resonant cavity 22 through passage 46 via inlet 44. The electromagnetic resonant cavity 22 is then cooled at constant pressure across a temperature range encompassing a solid-liquid equilibrium region or a solid-gas equilibrium region to directly detect solids formation.

Concurrently, the electromagnetic resonant cavity 22 is excited by microwave radiation by the microwave probes 52 and the response (i.e. the resonant frequency) of said cavity 22 is measured.

Typically, the resonant frequency of said cavity 22 responds approximately linearly with temperature, with a change in slope indicating solids formation in the cavity 22, in particular in the well 28. The frequency signature representative of solids formation often results in a rapid decrease in frequency, although exception to this trend may occur depending on the composition and morphology of the solids formed. The measurement of the resonant frequency allows relatively small changes in the resonant behaviour of the cavity to be detected.

Subsequent to a solids formation event, the solids may be purged from the well 28 and said cavity 22 by directing a stream of fluid through the passage 46 via inlet 44. Fluid egress from said cavity 22 is via outlets 48.

It will be well understood by those skilled in the art that the temperature of solidification ($T_{freeze}$) of the fluid or the bulk fluid composition may be determined with thermodynamic simulation programs for solid liquid equilibrium (SLE) calculations. Such thermodynamic simulation programs include, but are not limited to, Multiflash or thermodynamic calculation programs implemented within multiphase flow simulation programs OLGA, LedaFlow, HyFAST and CryoFAST. A particularly suitable example includes ThermoFAST which is specifically developed for predicting solid-liquid transitions in hydrocarbon mixtures. This thermodynamic simulation program has been endorsed by the Gas Processor Association Midstream organisation as a useful predictive tool for the thermodynamic properties of natural gas and LNG systems including solid-liquid equilibrium.

Advantageously, the apparatus 10 for directly detecting solids formation as described above may be readily utilised to determine the temperature of solidification ($T_{freeze}$) more accurately than may be predicted by such thermodynamic simulation programs discussed above.

In some dynamic systems where the bulk fluid is cooled, however, underlying changes in the bulk fluid's dielectric properties may mask deviations in resonance frequency caused by solids formation of freezable compounds. This is particularly relevant for fluids having trace impurities, where the amount and rate of solids formation may be low. While not wishing to be bound by theory, the inventors also opine that the crystal morphology of some freezable compounds may also play a role in this 'masking phenomenon'.

The inventors have discovered that this 'masking phenomenon' may be overcome by measuring changes to the dielectric permittivity ($\Delta\varepsilon$) of the fluid, as a function of the difference between a theoretical dielectric permittivity ($\varepsilon_{calc}$) of the bulk fluid and a measured dielectric permittivity ($\varepsilon_{meas}$) of the fluid, according to formula (1):

$$\Delta\varepsilon = \varepsilon_{meas} - \varepsilon_{calc}, \quad (1)$$

The measured dielectric permittivity ($\varepsilon_{meas}$) of the fluid is unitless and may be calculated as a function of the measured electromagnetic resonance frequency of the cavity ($f_{meas}$) in the presence of the fluid relative to the electromagnetic resonance frequency of the cavity measured under vacuum ($f_{vacuum}$), according to formula (2).

$$\varepsilon_{meas} = (f_{vacuum}/f_{meas})^2 \quad (2)$$

The theoretical dielectric permittivity ($\varepsilon_{calc}$) of the bulk fluid may be calculated with thermodynamic simulation programs for solid liquid equilibrium (SLE) calculations as described above, in particular ThermoFAST software, for known temperature and pressure conditions.

Measurement of changes in the dielectric permittivity ($\Delta\varepsilon$) of the fluid removes the systematic effect of changing bulk fluid dielectric properties by subtracting a theoretical dielectric permittivity ($\varepsilon_{calc}$) for the bulk fluid, calculated using fluid property software and the measured temperature and pressure, from the directly measured dielectric permittivity ($\varepsilon_{meas}$), calculated from the measured frequency shift of the cavity's resonance from the cavity's baseline frequency under vacuum. Using this null measurement algorithm, the presence of solids is identified as a deviation from zero or a baseline value.

The solidification temperature $T_{freeze}$ may be determined as the temperature at which the change in dielectric permittivity ($\Delta\varepsilon$) of the fluid deviates from a baseline value. This method of determining $T_{freeze}$ is also more accurate than the thermodynamic simulation programs discussed above. Notably, the solidification temperature $T_{freeze}$ determined by measuring the change in dielectric permittivity ($\Delta\varepsilon$) of the fluid coincides with the solidification temperature $T_{freeze}$ determined by measuring the resonance frequency of the cavity Determination of $T_{freeze}$ by cooling a fluid containing freezable solids in the apparatus 10 as described herein by measuring resonance frequency of the cavity or changes in dielectric permittivity ($\Delta\varepsilon$) of the fluid will now be described with reference to FIGS. 5a, 5b, 6a and 6b.

Figure 5A:
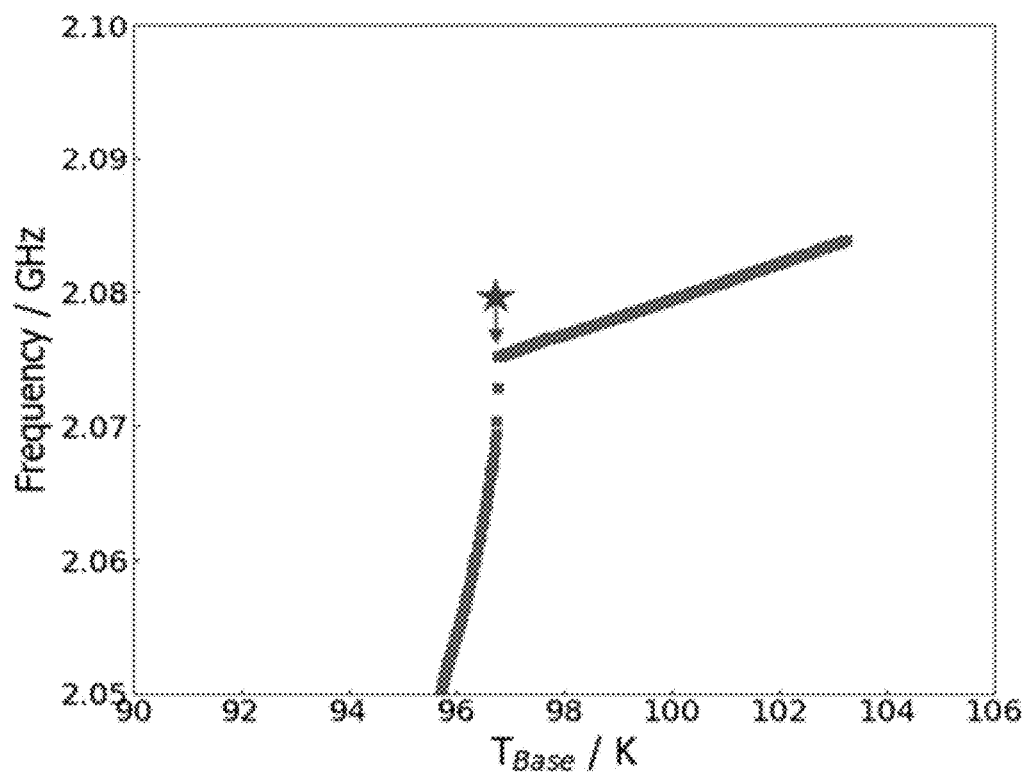
FIGS. 5a and 5b are graphical representations of measured resonance frequency and changes to dielectric permittivity of the fluid, respectively, with temperature for a mixture of 100 ppm $CO_2$ in methane.
Figure 5B:
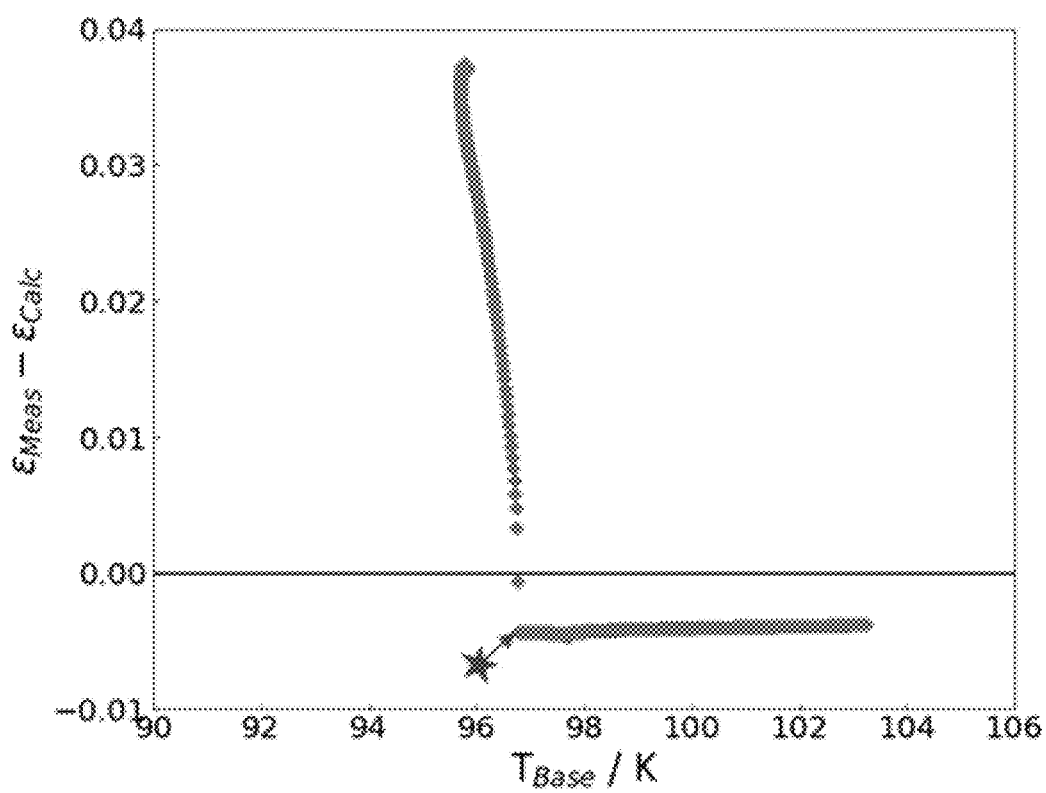

Referring to FIGS. 5a and 5b, the liquefaction temperature of pure methane and the solidification temperature $T_{freeze}$ predicted by SLE calculations using ThermoFAST for a mixture of 100 ppm $CO_2$ in methane at 9.5 MPa was 90.9 K and 103.5 K, respectively.

The mixture was cooled at a rate of 1 K/min from 110 K to 96 K, then held constant. FIG. 5a shows that there was a deviation from a linear relationship between temperature and measured resonance frequency of the cavity at 97.0 K, showing a clear signal of solids formation at $T_{freeze}=97.0$ K (indicated by the star). Similarly, FIG. 5b shows that there was a deviation from a baseline value with respect to change in dielectric permittivity ($\Delta\varepsilon$) of the fluid at 97.0 K, showing a clear signal of solids formation at $T_{freeze}=97.0$ K (indicated by the star). Both these measurements compared well with a visual identification of solids formation at 95.5 K for the same mixture at 10 MPa. Notably, both methods of determining $T_{freeze}$ were the same and 6.5 K lower than $T_{freeze}$ predicted by ThermoFAST.

Figure 6A:
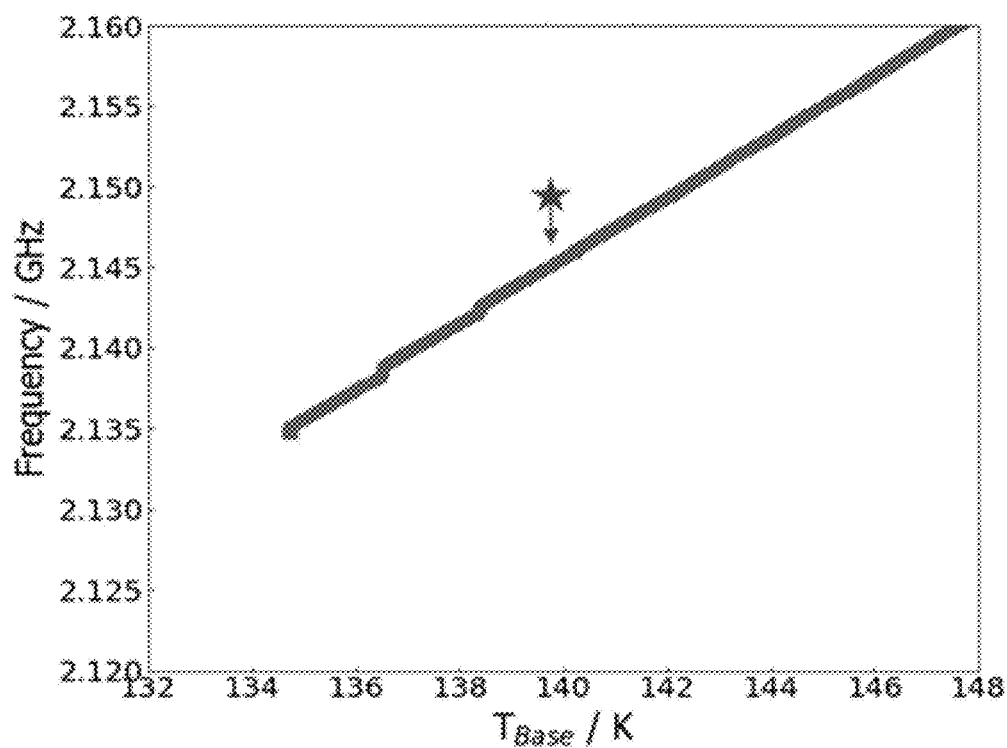
FIGS. 6a and 6b are graphical representations of measured resonance frequency and changes to dielectric permittivity of the fluid, respectively, with temperature for a mixture of 100 ppm benzene in methane.
Figure 6B:
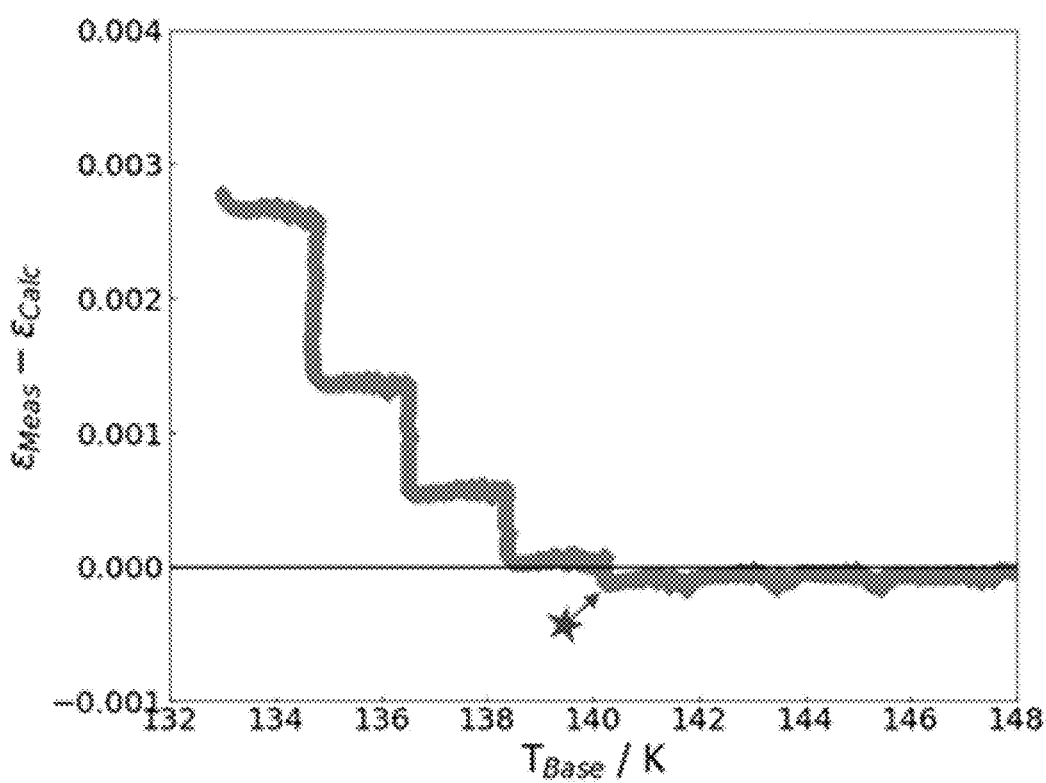

Referring to FIGS. 6a and 6b, the liquefaction temperature of pure methane and the solidification temperature $T_{freeze}$ predicted by SLE calculations using ThermoFAST for a mixture of 100 ppm benzene in methane at 9.5 MPa was 90.9 K and 149.7 K, respectively.

The mixture was cooled at a rate of 1 K/min from 148 K to 134 K, then held constant. FIG. 6a shows that there was no deviation from a linear relationship between temperature and measured resonance frequency of the cavity over the temperature range, even in the presence of solids, and therefore it was not possible to identify $T_{freeze}$. On the other hand, FIG. 6b shows that there was a deviation from a baseline value with respect to change in dielectric permittivity ($\Delta\varepsilon$) of the fluid at 140.1 K, showing a clear signal of solids formation at $T_{freeze}=140.1$ K (indicated by the star). Measured $T_{freeze}$ was 9.6 K lower than $T_{freeze}$ predicted by ThermoFAST.

Said apparatus 10 may find general application in determining the pressure and/or temperature at which solids form in a fluid of uncertain composition. In particular, said apparatus may be useful to determine the temperature at which solids form in contaminated natural gas as it passes through a cryogenic heat exchanger, and thereby determine an operating temperature to avoid solid blockages in the cryogenic heat exchanger.

Figure 7:
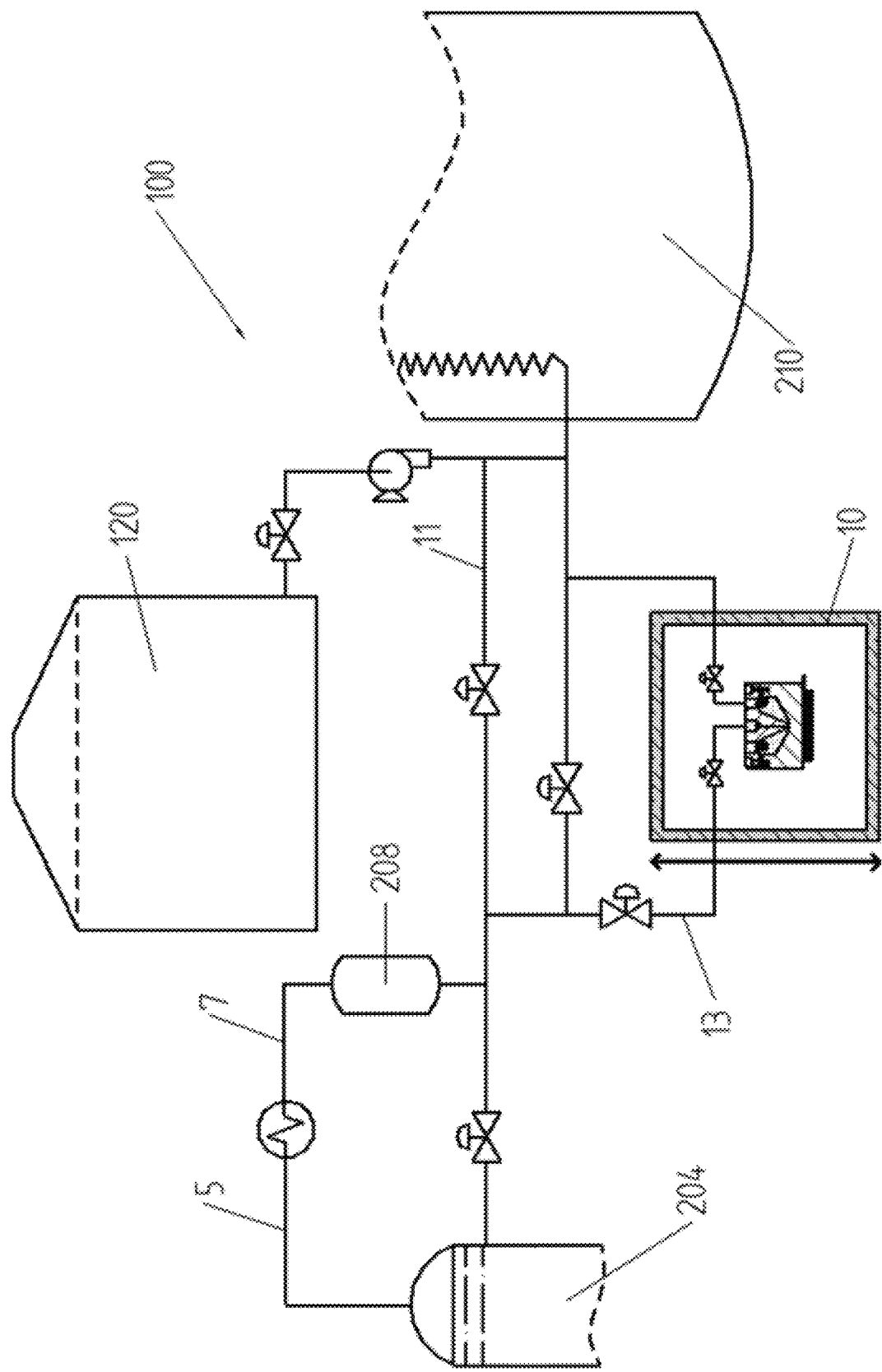
FIG. 7 is a schematic partial representation of the apparatus depicted in FIGS. 3a and 3b configured with respect to a cryogenic heat exchanger in accordance with various embodiments of the disclosure.

For example, said apparatus 10 may be conveniently configured with respect to the cryogenic heat exchanger to provide real time measurement of a sample of feed fluid and to directly detect solids formation and determine the temperature of solidification ($T_{freeze}$) before the feed fluid enters the cryogenic heat exchanger. The sample of feed fluid may be directed to said apparatus 10 via a bleed line as shown in FIG. 7 (as described below). Measurements may be taken intermittently or quasi-continuously to determine ($T_{freeze}$) as an absolute condition or compared in a relative sense to a plurality of samples investigated over a pre-determined period of time. For example, an increase in ($T_{freeze}$) with time may allude to changing feed fluid composition or inefficiencies in upstream units, for example heavy hydrocarbon removal units. Additionally, the magnitude of the signal response to solidification may also provide operators with a qualitative indication relating to the severity of solids formation downstream.

System and Method to Prevent or Remediate Solids Deposition in a Cryogenic Heat Exchanger In respect of LNG production, there are practical difficulties in measuring the specific composition of heavy hydrocarbons in natural gas entering the main cryogenic heat exchanger ('MCHE'), and therefore it is difficult to ascertain whether the fluid contains appreciable amounts of freezable compounds. Consequently, LNG plants are generally operated with a significant margin of safety to avoid potential solids deposition on the MCHE. This margin of safety is of an "open loop" nature.

The apparatus for directly detecting solids formation in a fluid disclosed herein enables measurement and control of an operating parameter not previously available: $\Delta T_{freeze}$. The solids formation temperature, $T_{freeze}$, may be obtained by taking a sample of fluid cooled by, or intended to be cooled by the cryogenic heat exchanger, and then progressively reducing the temperature of said sample until solids formation is detected. The parameter, $\Delta T_{freeze}$, is the difference between the operating temperature of the cryogenic heat exchanger $T_{liquid}$ and $T_{freeze}$ (i.e. $\Delta T_{freeze} = T_{liquid} - T_{freeze}$).

Integration of said apparatus as described herein in an LNG plant allows $\Delta T_{freeze}$ to be monitored so that corrective action may be initiated when $\Delta T_{freeze}$ varies from a predetermined operating margin. The predetermined operating margin may be from 1K to 20K, or from 1K to 10K, even from 2K to 5K. Said margin may vary depending on the historical stability of the cryogenic process. In this way, it becomes possible to control $\Delta T_{freeze}$ in a closed loop fashion.

Reliable knowledge of variation of $\Delta T_{freeze}$ from the predetermined operating margin and likelihood of solids deposition in the MCHE enables various units in the LNG plant that remove impurities (such as a heavy hydrocarbon removal unit) prior to the MCHE to be operated less conservatively. This means less gas is burnt to provide the energy necessary to remove the impurities, and hence overall plant efficiency is improved and a greater proportion of the gas entering the plant can be liquefied.

Figure 8:
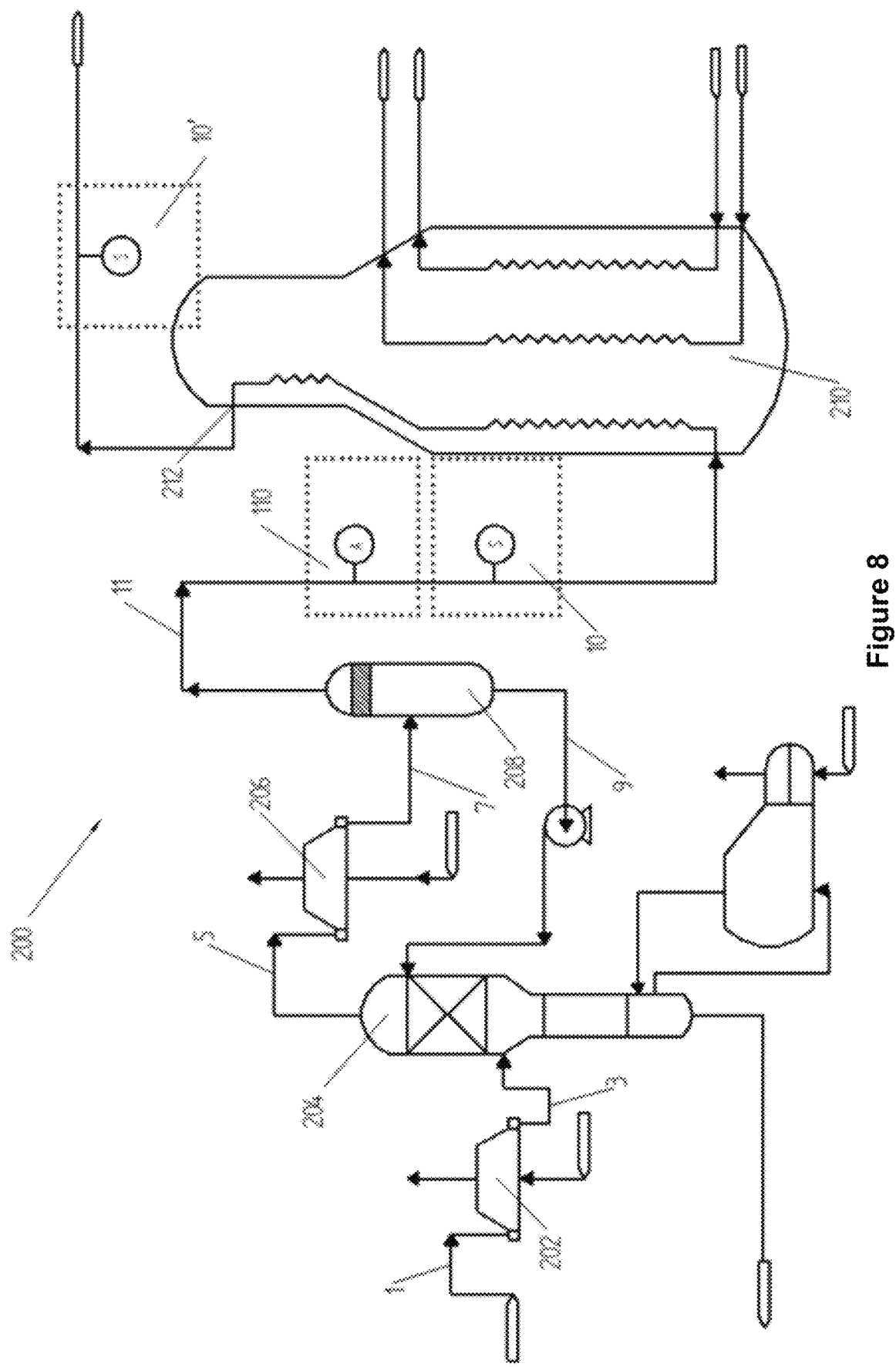
FIG. 8 is a schematic representation of an LNG processing plant integrated with a remediation system in accordance with various embodiments of the disclosure.

Referring to FIGS. 7 and 8, in accordance with various aspects of the present disclosure, there is shown a system 100 of remediating solids deposition ("the remediation system 100") in a cryogenic heat exchanger integrated with a natural gas liquefaction system 200. The natural gas liquefaction system 200 as described herein is described for illustrative purposes only and it will be appreciated that various embodiments of the remediation system 100 may be similarly integrated into alternative natural gas liquefaction systems 200 to facilitate remediation of solids deposition. Additionally, it will be appreciated that the remediation system 100 may be similarly integrated into a cryogenic gas liquefaction system for a gas other than natural gas, such as hydrogen, where impurities such as water, carbon dioxide, carbon monoxide or nitrogen may be present at sufficiently high concentrations to provide a risk of solids formation within the cryogenic heat exchanger.

A feed gas is introduced to the natural gas liquefaction system 200 via line 1 to a compressor 202 where the feed gas is compressed and subsequently cooled with a propane refrigerant. The cooled compressed feed gas is then fed via line 3 to a scrub column 204 for separation and removal of condensed heavy hydrocarbons ($C_{5+}$). A $C_{5+}$-depleted overhead vapour product of the scrub column 204 is passed via line 5 to compressor 206 where said overhead vapour product is compressed and subsequently cooled with a propane refrigerant. The compressed overhead vapour product is passed via line 7 to separator 208 to remove any condensed liquid hydrocarbons which are subsequently returned to the scrub column 204 via line 9.

An overhead vapour product of separator 208 ("gas stream") is then passed through a $C_{5+}$ analyser 110 via line 11. The $C_{5+}$ analyser 110 may be a gas chromatograph or any other suitable analyser that is capable of determining a cumulative content of heavy hydrocarbon compounds in the gas stream. Additional analysers (not shown) may also be provided to monitor the concentrations of other freezable compounds (e.g. water) which may freeze at cryogenic temperatures but which cannot be monitored by the gas chromatograph. It will be appreciated that the $C_{5+}$ analyser 110 may not be capable of determining a content of any one specific $C_{5+}$ compound in the gas stream from separator 208. Nevertheless, the skilled person will appreciate that such $C_{5+}$ analysers 110 may be capable of providing an estimate of the content of freezable hydrocarbon compounds, such as benzene content, as well as providing information about the composition of the gas stream.

The gas stream may then be passed via line 11 to a cryogenic heat exchanger 210 with cooling provided by one or more refrigerants (including mixed refrigerants) where the gas stream is cooled to an operating temperature ($T_{liquid}$) at or below the temperature at which the hydrocarbons in the overhead vapour product condense. Preferably, the gas stream is cooled to a temperature below the methane boiling point at an elevated pressure, for example to a temperature between about $-140°$ C. to $-150°$ C. The liquefied stream may be further expanded and cooled to about $-162°$ C. and atmospheric pressure for storage purposes.

Additionally, prior to entry to the cryogenic heat exchanger 210, a small sample of the gas stream may be passed via byline 13 to the apparatus 10 for detecting solids formation in a fluid. Said apparatus 10 may be used to directly detect solids formation and determine the temperature of solidification ($T_{freeze}$) for said sample, as described previously.

Detection of solids in said sample may be indicative that solids have formed (or will form) in the cryogenic heat exchanger 210. Accordingly, it is possible to correlate solids formation in said apparatus 10 with solids formation in the cryogenic heat exchanger 210.

The system 100 of the present disclosure may also include a thermodynamic simulation program for solid liquid equilibrium (SLE) calculations. Such thermodynamic simulation programs will be well understood by those skilled in the art and include, but are not limited to, Multiflash or thermodynamic calculation programs implemented within multiphase flow simulation programs OLGA, LedaFlow, HyFAST and CryoFAST. A particularly suitable example includes ThermoFAST which is specifically developed for predicting solid-liquid transitions in hydrocarbon mixtures. This thermodynamic simulation program has been endorsed by the Gas Processor Association Midstream organisation as a useful predictive tool for the thermodynamic properties of natural gas and LNG systems including solid-liquid equilibrium.

The composition of the gas stream, including the $C_{5+}$ content, measured by the gas chromatograph 110 may be used in the thermodynamic simulation program to determine a remedial composition capable of removing solids deposited in the cryogenic heat exchanger 210. In other words, the thermodynamic simulation program will determine the nature of the solvent in which the freezable compounds of interest are soluble or a variation in the composition in the fluid which would move the conditions of SLE to where the deposited solids would undergo a solid-liquid or solid-gas phase transition.

The temperature of solidification ($T_{freeze}$) determined by said apparatus 10 for directly detecting solids formation may be used in the thermodynamic simulation program to determine a remedial temperature ($T_{remedial}$) to remove solids deposited in the cryogenic heat exchanger 210.

The remediation system 100 may further include a temperature controller (not shown) for the cryogenic heat exchanger 210 to raise or lower the operating temperature of the cryogenic heat exchanger 210 to the remedial temperature ($T_{remedial}$) calculated by the thermodynamic simulation program. The temperature controller may be in operative communication with the cryogenic heat exchanger 210 to vary a refrigeration duty in one or more locations in the cryogenic heat exchanger 210 to raise or lower the operating temperature to the remedial temperature ($T_{remedial}$). Counterintuitively, in some embodiments, lowering the operating temperature of the cryogenic heat exchanger 210 may facilitate removal of solids (i.e. 'retrograde' melting) within the cryogenic heat exchanger 210, rather than increased solids deposition, because the solubility of the deposited solids in the fluid in the cryogenic heat exchanger 210 may increase with decreasing temperature.

Alternatively, or additionally, the remediation system 100 may also include a remedial fluid dosing means 120 to adjust the composition of the fluid in the cryogenic heat exchanger 210 to the remedial composition. The composition of the fluid may be adjusted to the remedial composition by injecting an amount of a remediation fluid into the gas stream prior to entry to the cryogenic heat exchanger 210. The remedial fluid may be injected continuously or at intermittent or regular intervals until the solids have been removed from the cryogenic heat exchanger 210.

The remediation fluid may comprise one or more hydrocarbon compounds that when added to the gas stream will increase the solubility of freezable compounds. It will be appreciated that the composition of the remediation fluid will vary according to the composition of the gas stream and the operating conditions of the cryogenic heat exchanger 210. Nevertheless, it is anticipated that the remediation fluid may be sourced from hydrocarbon fluids which may be conveniently available on site including, but not limited to, refrigerants such as propane refrigerant, heavy mixed refrigerants, light mixed refrigerants, or product fluids such as ethane, LPGs and light condensate and so forth.

Introduction of the remedial fluid into the gas stream will inherently and temporarily change the composition, and hence the energy properties, of the LNG produced in the cryogenic heat exchanger 210. Significant changes to the LNG composition, particularly if the LNG composition is 'off specification', may require the LNG to be recycled or flared. It is anticipated that the financial losses associated with flaring will be insignificant compared to losses that would be incurred from a complete plant shutdown to remove solids blockages which may require several days.

The remediation system 100 may optionally include a further apparatus 10' for detecting solids formation in fluid communication with an outlet 212 of the cryogenic heat exchanger 210 to monitor the effectiveness of the remediation process. A sample of output fluid from the outlet 212 from the cryogenic heat exchanger 210 may be passed through said apparatus 10' and the behaviour with respect to solids formation of said output fluid may be investigated across an operating temperature range of the cryogenic heat exchanger 210. The presence (or absence) of solids formation in said apparatus 10' may be correlated with the progress of the remediation process within the cryogenic heat exchanger 210, with presence of solids formation in said apparatus 10' indicating a need to continue the remediation process and an absence (or cessation) of solids formation in said apparatus 10' indicating a successful or completed remediation process.

The effectiveness of the remediation process may also be monitored by measuring a pressure drop across the cryogenic heat exchanger 210, whereby a decrease in the pressure drop may indicate the removal of the solids deposit therein.

It will be appreciated that prior to adjusting the feed gas composition to the remedial composition or raising or lowering the operating temperature to the remedial temperature ($T_{remedial}$), such remedial actions may first be tested in said apparatus 10 for detecting solids formation to gauge the effectiveness of such remedial actions before they are implemented with respect to the cryogenic heat exchanger 210.

Various embodiments may be illustrated by the following examples. The examples are provided for illustrative purposes only and are not to be construed as limiting the scope or content of the disclosure in any way.

Example 1

An electromagnetic resonant cavity 22 of the apparatus 10 as described herein was filled with a sample of 4% p-xylene, 96% ethane fluid and cooled from −60° C. to −82° C. at constant pressure with concurrent measurement of the resonant frequency response of said cavity.

Figure 9:
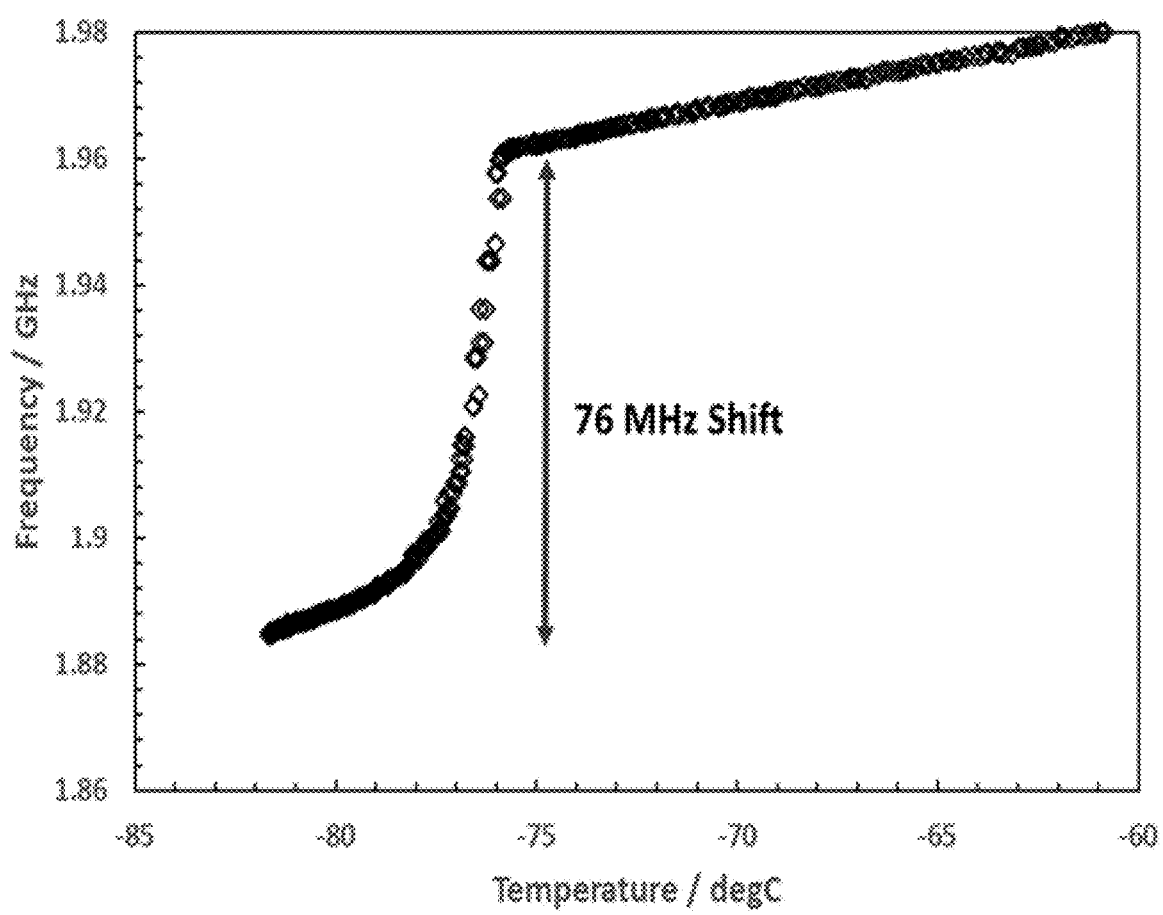
FIG. 9 is a graphical representation of resonant frequency measured with respect to temperature for a solution of 4% p-xylene in ethane.

FIG. 9 shows that a 76 MHz shift was observed at $T_{freeze}$ −76° C. at onset of solids formation which is consistent with FEA simulations. The smallest frequency shift that can be resolved is approximately 25 kHz which, through extrapolation, would suggest sensitivity to p-xylene solid at ~3 ppm by mole. FEA modelling of said cavity 22 may be combined with this data to estimate the smallest solid volume that the apparatus 10 is capable of detecting unambiguously. For the ethane p-xylene system, the apparatus 10 may detect a solids volume equivalent to 0.0001 v/v % of the volume of the cavity 20. This is significant given that the relative difference in dielectric properties of liquids and solids is small for hydrocarbons.

Example 2

Example 2 illustrates a case study in the remediation of a benzene solid deposition after the addition of three different remediation fluids (mixed refrigerant (MR), iso-butane (iC4) and neo-pentane (n-$C_5$) into the gas stream of the cryogenic heat exchanger. The results are based on the solubility of benzene in the remedial composition as predicted by the thermodynamic simulation tool ThermoFAST. The case study involves the deposition of 1 kg of benzene solid in the cryogenic heat exchanger, the composition of the gas stream and flow rates analogous with those experienced by RasGas Train 4 prior to the blockage event in November 2014. Table 2 provides the composition of the gas stream under normal operating conditions for this LNG train. The average mass flow rate flowing through the cryogenic heat exchanger is 146 kg/s with coldest effluent temperature of 124 K.

TABLE 2

Estimate of the molar composition of natural gas components in a gas stream fed to main cryogenic heat exchanger during normal operation at the RasGas plant.

| Component | Composition |
|---|---|
| Carbon dioxide | 0.00004 |
| Methane | 0.909329 |
| Ethane | 0.057492 |
| Propane | 0.021953 |
| Iso-Butane | 0.004239 |
| n-Butane | 0.006847 |
| Iso-Pentane | 0.000028 |
| n-Pentane | 0.000026 |
| Hexane | 0.000026 |
| Heptane | 0.000016 |
| Benzene | 0.000004 |

Figure 10A:
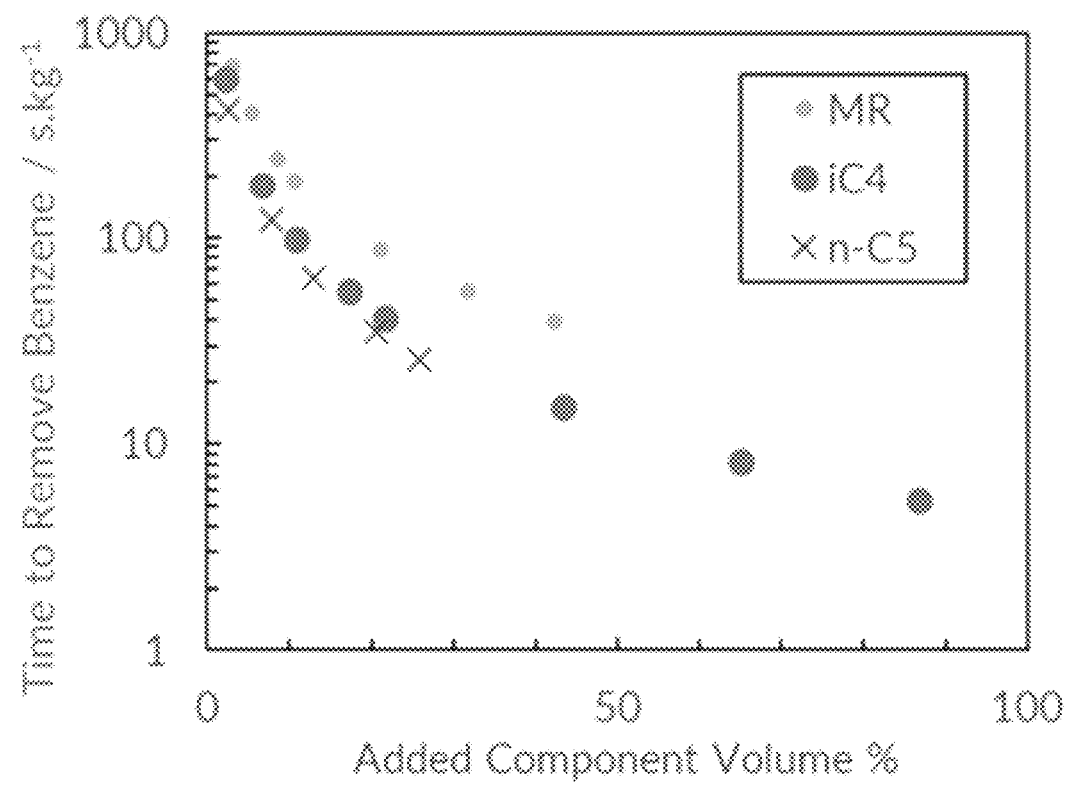
FIG. 10 a) is a graphical representation of time for removal of benzene solids as a function of the injected volume of three different remedial fluids, mixed refrigerant (MR); iso-butane ($iC_4$); and normal-pentane ($n-C_5$).
Figure 10B:
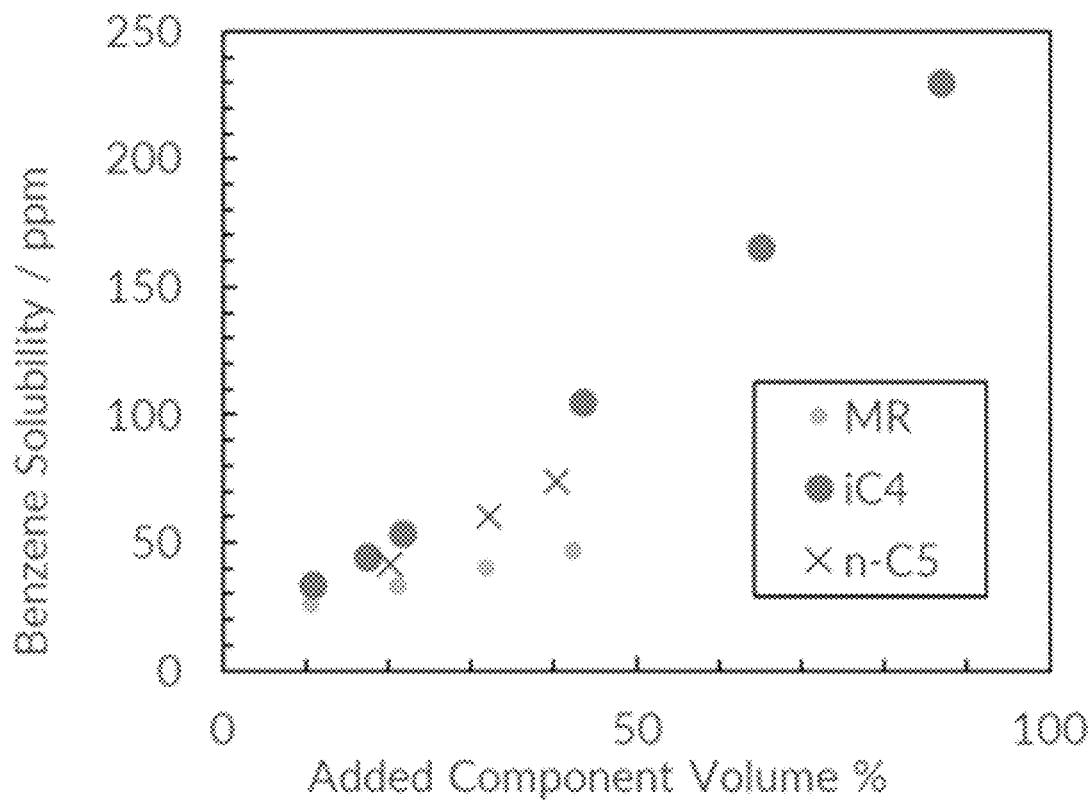

FIG. 10 a) illustrates the time of remedial fluid addition required to remove the benzene deposit per volume percent added of each component. It can be seen that some remedial fluids perform better per unit volume in the dissolution of benzene, however the optimum choice will depend on price and availability of the remedial fluids. Despite being the worst performer by volume, mixed refrigerant fluid is readily available and stored in large amounts in LNG plants.

FIG. 10 b) graphically represents the solubility of benzene in the adjusted composition of the gas stream given the addition of the remediation fluids. Intuitively the solubility of benzene increases with increased volume of remediation fluid added, however the amount added by an operator would be constrained by the plant's ability to cope with additional mass flow through its unit operations.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

In the claims which follow and in the preceding description except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An apparatus for directly detecting a solid formation in a fluid under known pressure and temperature conditions, the apparatus comprising:
   a vessel to receive the fluid, the vessel defining an electromagnetic resonant cavity, operating at frequencies up to and including microwave frequencies, with resonant properties sensitive to a presence of a solid phase;
   a heat exchanger and/or a thermoelectric cooler to vary a temperature of the vessel and the fluid therein;
   one or more probes for exciting and monitoring an electromagnetic resonance of the cavity;
   a pressure sensor and a temperature sensor for sensing the pressure and temperature respectively of fluid in the cavity; and
   a signal processor operatively connected to said pressure and temperature sensors and said one or more probes to directly detect the solid formation in the fluid within the cavity in response to detected changes to dielectric permittivity ($\Delta\varepsilon$) of the fluid therein;
   wherein changes to the dielectric permittivity of the fluid ($\Delta\varepsilon$) are calculated according to:

$$\Delta\varepsilon = \varepsilon_{meas} - \varepsilon_{calc}, \quad (1)$$

wherein, for the known temperature and pressure, Scale is a theoretical dielectric permittivity of a bulk fluid, and $\varepsilon_{meas}$ is calculated according to:

$$\varepsilon_{meas} = (f_{vacuum}/f_{meas})^2 \quad (2)$$

wherein, for the known temperature and pressure, $f_{vacuum}$ is the electromagnetic resonance frequency of the cavity under vacuum and $f_{meas}$ is the electromagnetic resonance frequency of the cavity in the presence of the fluid;
   wherein the electromagnetic resonant cavity is defined by:
   an upper portion and a lower portion of the vessel having a gap defined therebetween, the gap having resonant properties sensitive to the presence of the solid phase, wherein the upper portion or the lower portion is provided with a passage extending therethrough in fluid communication with an inlet to allow ingress of a stream of fluid to the gap and thereby purge the solid formation from the cavity subsequent to the detection of the solid formation.

2. The apparatus as defined in claim 1, wherein the lower portion is configured to define a well and favor the solid formation therein.

3. The apparatus as defined in claim 2, wherein the well is integral with a co-axially aligned spigot extending through the lower portion, the spigot being fabricated from a material having a higher thermal conductivity than a surrounding area of the lower portion, said spigot thereby being capable of providing a thermal gradient between the well and said surrounding area to favor the solid formation in the well.

4. The apparatus as defined in claim 3, wherein the lower portion is in heat exchange communication with the heat exchanger and/or the thermoelectric cooler to cool the resonant cavity.

5. The apparatus as defined in claim 3, wherein said spigot is in heat exchange communication with a second heat exchanger and/or thermoelectric cooler, wherein the second heat exchanger and/or the thermoelectric cooler are arranged, in use, to cool the well to a lower temperature than the surrounding area of the lower portion.

6. The apparatus as defined in claim 2, wherein the lower portion defines a cylindrical side wall and a sloping bottom wall terminating in the well, wherein the well is co-axially aligned with the cylindrical side wall, and the upper portion defines an annular top wall and a protrusion co-axially aligned with the well, wherein said gap is defined between the protrusion and the well.

7. The apparatus as defined in claim 6, wherein the passage extends through said protrusion.

8. The apparatus as defined in claim 6, wherein the passage extends through the well.

9. The apparatus as defined in claim 1, wherein the passage is dimensioned to allow the stream of fluid to flow directly to the gap.

10. The apparatus as defined in claim 1, wherein a resonant frequency of said cavity is tuned by varying a size of the gap.

11. A system to prevent or remediate a solid deposition in a cryogenic heat exchanger, said system comprising:
the cryogenic heat exchanger for cooling the fluid to a liquid at an operating temperature ($T_{liquid}$);
an apparatus to directly detect the solid formation as defined in claim 1, wherein said apparatus is configured to receive a sample of the fluid cooled, or intended to be cooled, by the cryogenic heat exchanger and determine a temperature ($T_{freeze}$) corresponding to a temperature at which the solid formation forms in the fluid and $\Delta T_{freeze}$ wherein $\Delta T_{freeze} = T_{liquid} - T_{freeze}$; and
a controller in operative communication with the cryogenic heat exchanger whereby, in use, the controller is arranged to initiate corrective action when $\Delta T_{freeze}$ is less than a predetermined operating temperature margin.

12. The system as defined in claim 11, wherein the controller is arranged to initiate corrective action by raising or lowering the operating temperature ($T_{liquid}$) of the cryogenic heat exchanger or by introducing a remedial fluid in the cryogenic heat exchanger.

13. The system as defined in claim 11, further comprising:
an analyser to determine a composition of the fluid;
a thermodynamic simulation program for solid liquid equilibrium (SLE) calculations, said program being arranged to use ($T_{freeze}$) and the composition of the fluid to calculate a remedial temperature ($T_{remedial}$) to remove the solid deposition solids deposited in the cryogenic heat exchanger; and
a temperature controller in operative communication with the controller to raise or lower the operating temperature of the cryogenic heat exchanger to the remedial temperature ($T_{remedial}$).

14. The system as defined in claim 13, wherein the temperature controller is in operative communication with the cryogenic heat exchanger to vary a refrigeration duty in one or more locations in the cryogenic heat exchanger to raise or lower the operating temperature to the remedial temperature ($T_{remedial}$).

15. The system as defined in claim 11, further comprising:
an analyser to determine a composition of the fluid;
a thermodynamic simulation program for solid liquid equilibrium (SLE) calculations, said program being arranged to use ($T_{freeze}$) and the composition of the fluid to calculate a remedial composition capable of dissolving the solid deposition deposited in the cryogenic heat exchanger; and
remedial fluid inlet in operative communication with the controller to introduce the remedial fluid into the cryogenic heat exchanger in an amount sufficient to achieve the remedial composition.

16. The system as defined in claim 11, wherein said system further comprises a second sensor to directly detect the solid formation as defined in claim 1, said second sensor being arranged in fluid communication with an outlet of the cryogenic heat exchanger to monitor an effectiveness of remediation.

17. A method of preventing or remediating a solid deposition in a cryogenic heat exchanger arranged, in use, to cool the fluid to a liquid at an operating temperature ($T_{liquid}$), the method comprising the steps of:
directly detecting the solid formation in a sample of fluid cooled by, or intended to be cooled by, the cryogenic heat exchanger and determining a temperature ($T_{freeze}$) corresponding to a temperature at which the solid formation forms in the fluid and $\Delta T_{freeze}$ wherein $\Delta T_{freeze} = T_{liquid} - T_{freeze}$, wherein the step of detecting the solid formation is performed by using the apparatus for detecting the solid formation as defined in claim 1; and
initiating corrective action for operating the cryogenic heat exchanger when $\Delta T_{freeze}$ is less than a predetermined operating temperature margin.

\* \* \* \* \*